US012569500B2

(12) United States Patent
Wu et al.

(10) Patent No.: US 12,569,500 B2
(45) Date of Patent: Mar. 10, 2026

(54) COMBINATION COMPRISING TRICYCLE COMPOUND AND USE THEREOF IN PREPARATION OF MEDICAMENT FOR TREATING HBV

(71) Applicant: FUJIAN AKEYLINK BIOTECHNOLOGY CO., LTD., Fujian (CN)

(72) Inventors: Wenqiang Wu, Fujian (CN); Dong Zhang, Fujian (CN); Zhiqiang Ma, Fujian (CN); Yixin Zhou, Fujian (CN); John Mao, Fujian (CN); Zhigan Jiang, Shanghai (CN); Jing Wang, Shanghai (CN); Haiying He, Shanghai (CN)

(73) Assignee: FUJIAN AKEYLINK BIOTECHNOLOGY CO., LTD., Fujian (CN)

( * ) Notice: Subject to any disclaimer, the term of this patent is extended or adjusted under 35 U.S.C. 154(b) by 636 days.

(21) Appl. No.: 17/925,075

(22) PCT Filed: May 14, 2021

(86) PCT No.: PCT/CN2021/093769
§ 371 (c)(1),
(2) Date: Nov. 14, 2022

(87) PCT Pub. No.: WO2021/228213
PCT Pub. Date: Nov. 18, 2021

(65) Prior Publication Data

US 2023/0190768 A1 Jun. 22, 2023

(30) Foreign Application Priority Data

May 15, 2020 (CN) ........................ 202010412760.9
Dec. 31, 2020 (CN) ........................ 202011633373.4

(51) Int. Cl.
*A61K 31/554* (2006.01)
*A61K 31/513* (2006.01)
(Continued)

(52) U.S. Cl.
CPC .......... *A61K 31/554* (2013.01); *A61K 31/513* (2013.01); *A61K 31/522* (2013.01);
(Continued)

(58) Field of Classification Search
CPC .............. A61K 2300/00; A61K 31/513; A61K 31/522; A61K 31/5365; A61K 31/553;
(Continued)

(56) References Cited

U.S. PATENT DOCUMENTS 10,239,872 B2 * 3/2019 Chen .................... C07D 498/04
11,053,260 B2 * 7/2021 He .......................... A61P 31/12

FOREIGN PATENT DOCUMENTS

CN 102060786 A 5/2011
CN 105102451 A 11/2015
(Continued)

OTHER PUBLICATIONS

Extended European Search Report issued in European Patent Application No. 21804833.8 dated Oct. 17, 2023.
(Continued)

*Primary Examiner* — Savitha M Rao
(74) *Attorney, Agent, or Firm* — SZDC Law PC

(57) ABSTRACT

A combination comprising a tricycle compound and use thereof in the preparation of a medicament for treating HBV. The combination is a combination of a compound of formula (I) or a pharmaceutically acceptable salt thereof and any one drug in the following groups a-c: a. a hepatitis B surface antigen inhibitor, b. a reverse transcriptase inhibitor, and c. a hepatitis B surface antigen inhibitor and a reverse transcriptase inhibitor.
(Continued)

95% confidence space synergy/antagonism effect map

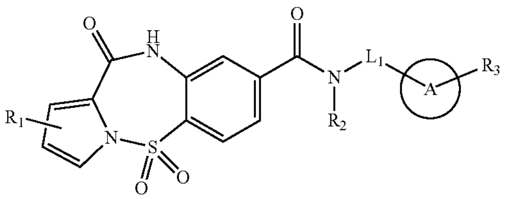

(I)

19 Claims, 3 Drawing Sheets

(51) Int. Cl.

| | |
|---|---|
| ***A61K 31/522*** | (2006.01) |
| ***A61K 31/5365*** | (2006.01) |
| ***A61K 31/553*** | (2006.01) |
| ***A61K 31/675*** | (2006.01) |
| ***A61K 45/06*** | (2006.01) |
| ***A61P 31/20*** | (2006.01) |

(52) U.S. Cl.
CPC ........ *A61K 31/5365* (2013.01); *A61K 31/553* (2013.01); *A61K 31/675* (2013.01); *A61K 45/06* (2013.01); *A61P 31/20* (2018.01)

(58) Field of Classification Search
CPC ................ A61K 31/554; A61K 31/675; A61K 31/683; A61K 45/06; A61P 1/16; A61P 31/20
See application file for complete search history.

(56) References Cited

FOREIGN PATENT DOCUMENTS

| | | | |
|---|---|---|---|
| CN | 106255684 | A | 12/2016 |
| CN | 106459032 | A | 2/2017 |
| EP | 3632914 | A1 | 4/2020 |
| JP | 2019501202 | A | 1/2019 |
| JP | 2019511542 | A | 4/2019 |
| JP | 2019526562 | A | 9/2019 |
| WO | 2017120527 | A2 | 7/2017 |
| WO | 2017181141 | A2 | 10/2017 |
| WO | 2018036941 | A1 | 3/2018 |
| WO | 2018153285 | A1 | 8/2018 |
| WO | 2018161960 | A1 | 8/2018 |
| WO | 2018214875 | A1 | 8/2018 |
| WO | 2020038456 | A1 | 2/2020 |

OTHER PUBLICATIONS

Aziz Muneba et al: "Predictors of Therapeutic Outcome to Nucleotide Reverse Transcriptase Inhibitor in Hepatitis B Patients", Viral Immunology, 2018,9 (31), pp. 632-638.
Yang L et al: "Identification and Characterization of Pyrimidinediones as Potent Non-nucleoside Reverse Transcriptase Inhibitors of Hepatitis B virus", Antiviral Research. Elsevier BV. NL, 2009,2,(82), p. A32.
1st Chinese Office Action issued in Chinese Patent Application No. CN2021800342172 dated Jan. 18, 2024.
Chinese Search Report issued in Chinese Patent Application No. CN2021800342172 dated Jan. 11, 2024.
International Search Report issued in International Patent Application No. PCT/CN2021/093769 dated Aug. 12, 2021.
Written Opinion of the International Searching Authority issued in International Patent Application No. PCT/CN2021/093769 dated Aug. 12, 2021.
Wang Hongliang, et al. "Anti-hepatitis B virus drugs: research advances", International Journal of Pharmaceutical Research, 43(1), pp. 134-138 (Feb. 29, 2019).
2nd -Chinese Office Action dated May 27, 2024 issued in Chinese Patent Application No. CN2021800342172.
Chinese Search Report dated May 27, 2024 issued in Chinese Patent Application No. CN2021800342172.
Hongzhou Lu et al., "Common drugs and interactions of AIDS and related diseases". Shanghai Scientific and Technical Publishers, pp. 15-16, 2020.
Youwen Tan, "liver disease said by Lao Tan". Soochow University Press, pp. 14, 2019.
Chinese Rejection Decision dated Jan. 8, 2025 issued in Chinese Patent Application No. CN 202180034217.2.
First Office Action dated Mar. 4, 2025 issued in Japanese Patent Application No. JP 2022570093.
Office Communication dated Aug. 21, 2025 from European Patent Application No. 221804833.8.

* cited by examiner

COMBINATION COMPRISING TRICYCLE COMPOUND AND USE THEREOF IN PREPARATION OF MEDICAMENT FOR TREATING HBV

The present application is the National Stage Application of PCT/CN2021/093769, filed on May 14, 2021, which claims the priorities of Chinese Patent Application No. CN202010412760.9 filed on May 15, 2020 and Chinese Patent Application No. CN202011633373.4 filed on Dec. 31, 2020, and the contents of which are incorporated herein by reference in their entireties.

TECHNICAL FIELD

The present disclosure relates to a pharmaceutical combination, and in particular to a compound with a three fused ring structure or a pharmaceutically acceptable salt thereof, and optionally a combination comprising one or two of a hepatitis B surface antigen inhibitor and/or a reverse transcriptase inhibitor, and use of the combination in the manufacture of a medicament for treating hepatitis B. Specifically, the present disclosure discloses a compound of formula (I) or a pharmaceutically acceptable salt thereof, and optionally a combination comprising one or two of a hepatitis B surface antigen inhibitor and/or a reverse transcriptase inhibitor, and use of the combination in the manufacture of a medicament for treating hepatitis B.

BACKGROUND

Hepatitis B is an inflammatory response caused by hepatitis B virus invasion, which can lead to a series of disorders such as liver pain, hepatosplenomegaly, liver fibrosis, severe cirrhosis and even liver cancer. According to statistics, there are about 350-400 million carriers of hepatitis B virus in the world, and one third of them are in China. In China, the number of deaths caused by hepatitis B reaches up to 500,000 per year.

At this stage, there is no efficacious drug to cure hepatitis B in the world. The first-line drugs for hepatitis B treatment in China are mainly nucleoside drugs, interferon and traditional Chinese medicine, which are accompanied with problems such as high cost and easy recurrence. Therefore, the development of a new type of anti-hepatitis B drug is imperative. Due to the problems that drug resistance and unsatisfactory treatment effect of single drug therapy of the existing drugs cannot be well solved, the combination use of drugs for treating hepatitis B, especially the combination use of drugs for treating hepatitis B with different mechanisms, is becoming a concern of research and a direction of clinical use increasingly.

The Patent WO2018153285A1 discloses a compound of formula (I) and use thereof, wherein the compound is a hepatitis B core protein inhibitor; the Patents WO2018214875A1 and WO2018161960A1 disclose hepatitis B surface antigen inhibitors of a compound of formula (II) and a compound of formula (III) and use thereof, respectively. Nucleoside or nucleotide reverse transcriptase inhibitors which are recommended to be used clinically at present include entecavir, tenofovir disoproxil fumarate and the like. The present disclosure aims to achieve the purpose of treating HBV in a synergistic manner by combining and using drugs with different mechanisms.

CONTENT OF THE PRESENT INVENTION

The present disclosure discloses a pharmaceutical combination, wherein the combination is a compound of formula (I) or a pharmaceutically acceptable salt thereof (I)

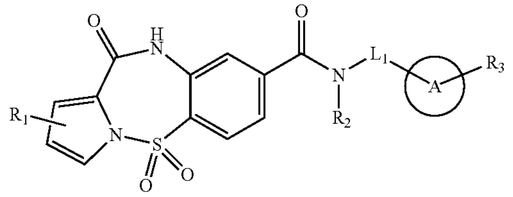

and a combination of any one of the following groups a to c of drugs:

a. a hepatitis B surface antigen inhibitor, b. a reverse transcriptase inhibitor, and c. a hepatitis B surface antigen inhibitor and a reverse transcriptase inhibitor, wherein, in formula (I), $L_1$ is a single bond or —$C_{1-6}$ alkyl;

$R_1$ is H, Cl, F, Br, I, or $C_{1-3}$ alkyl optionally substituted with 1, 2 or 3 $R_a$;

ring A is 4-8 membered heterocycloalkyl or $C_{3-8}$ cycloalkyl;

$R_2$ is H and $C_{1-3}$ alkyl;

$R_3$ is H and $C_{1-3}$ alkyl;

$R_a$ is each independently H, F, Cl, Br, I, $NH_2$, OH, CN, $C_{1-6}$ alkyl or $C_{1-6}$ heteroalkyl, or $C_{1-6}$ alkyl and $C_{1-6}$ heteroalkyl optionally substituted with 1, 2 or 3 R';

R' is each independently selected from: Cl, F, Br, I, $NH_2$, $CH_3$, CN and —$N(CH_3)_2$;

the 4-8 membered heterocycloalkyl and $C_{1-6}$ heteroalkyl each comprise 1, 2, 3 or 4 heteroatoms or heteroatom groups independently selected from —O—, —NH—, —S— and N.

Preferably, wherein $R_a$ is each independently H, F, Cl, Br, I, $NH_2$, OH or CN.

Where ring A is 5-6 membered heterocycloalkyl.

Where ring A is tetrahydrofuryl, tetrahydropyranyl or dioxanyl.

Where ring A is

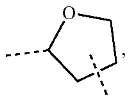 , 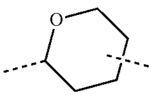 or 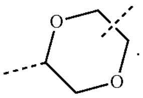 .

Where $R_1$ is H, Cl, F, Br, I, or $CH_3$ optionally substituted with 1, 2 or 3 $R_a$. More preferably, $R_1$ is H, Cl or $CH_3$.

Where $R_2$ is H or $CH_3$.

Where $R_3$ is H or $CH_3$.

Where $L_1$ is —$CH_2$— or —$CH_2CH_2$—.

In one embodiment, wherein the compound of formula (I) has a structure shown as formula (I-1):

(I-1)

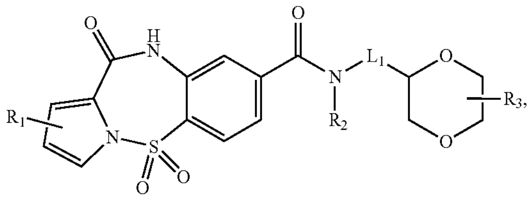

wherein $R_1$, $R_2$, $R_3$ and $L_1$ are as defined above.

The particularly preferred compound of formula (I) of the present disclosure is selected from the following specific compounds:

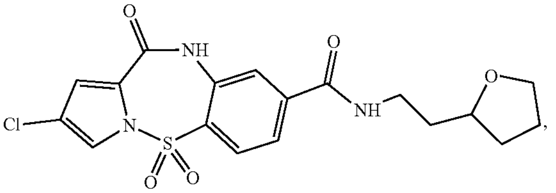

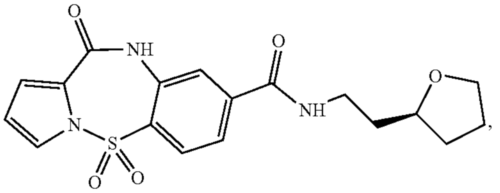

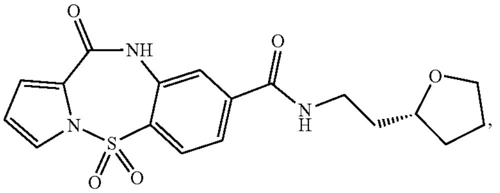

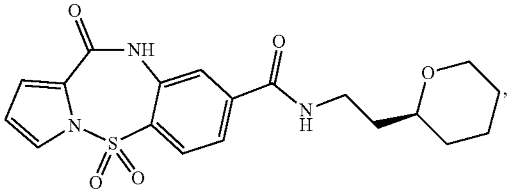

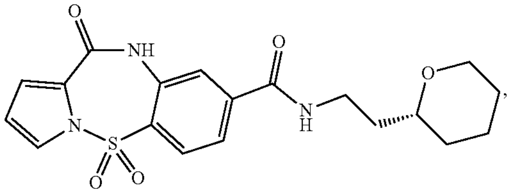

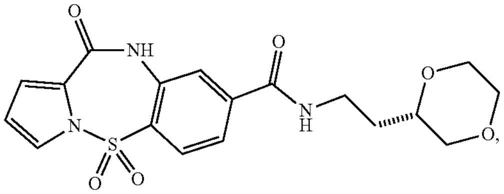

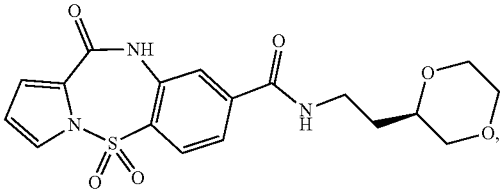

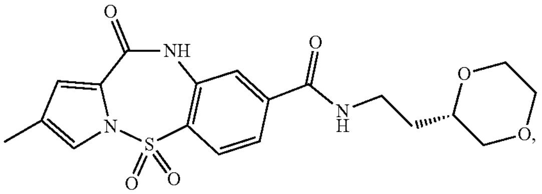

-continued

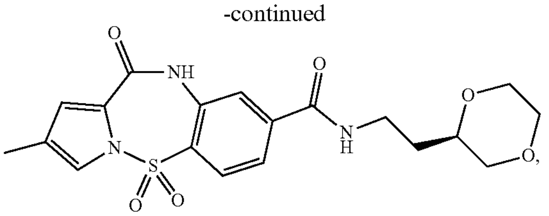

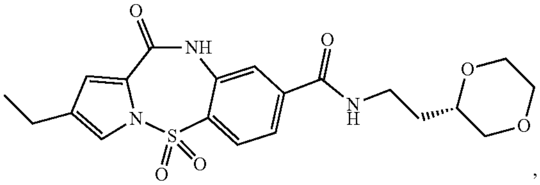

, or

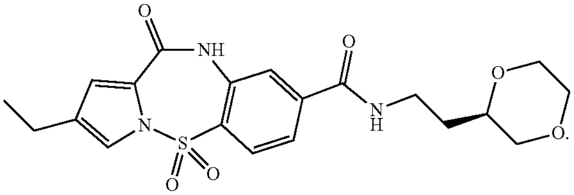

In some embodiments of the present disclosure, for above combination, the hepatitis B surface antigen inhibitor is selected from one of the compounds of formula (II)

(II)

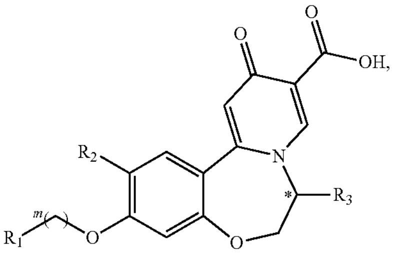

or a pharmaceutically acceptable salt thereof, wherein, $R_1$ is selected from: H, OH, CN, $NH_2$, or from the following groups optionally substituted with 1, 2 or 3 R: $C_{1-6}$ alkyl, $C_{1-6}$ heteroalkyl, $C_{2-5}$ alkenyl, $C_{2-5}$ heteroalkenyl, $C_{3-6}$ cycloalkyl or 3-6 membered heterocycloalkyl;

$R_2$ is selected from: H, OH, CN, $NH_2$, halogen, or from the following groups optionally substituted with 1, 2 or 3 R: $C_{1-3}$ alkyl, $C_{1-3}$ heteroalkyl, $C_{3-6}$ cycloalkyl or 3-6 membered heterocycloalkyl;

$R_3$ is selected from the following groups optionally substituted with 1, 2 or 3 R: $C_{1-6}$ alkyl and $C_{3-6}$ cycloalkyl;

m is selected from: 0, 1, 2, 3, 4 or 5;

when m is 0, $R_1$ is not selected from: OH, CN and $NH_2$;

R is selected from: H, halogen, OH, CN, $NH_2$, or from the following groups optionally substituted with 1, 2 or 3 R': $C_{1-3}$ alkyl and $C_{1-3}$ heteroalkyl;

R' is selected from: F, Cl, Br, I, OH, CN, $NH_2$, $CH_3$, $CH_3CH_2$, $CH_3O$, $CF_3$, $CHF_2$ and $CH_2F$;

"hetero" represents a heteroatom or a heteroatom group, and the "hetero" in $C_{1-6}$ heteroalkyl, $C_{2-5}$ heteroalkenyl, 3-6 membered heterocycloalkyl and $C_{1-3}$ heteroalkyl is each independently selected from: —C(═O)N(R)—, —N(R)—, —C(═NR)—, —(R)C═N—, —S(═O)$_2$N(R)—, —S(═O)N(R)—, N, —O—, —S—, ═O, ═S, —C(═O)O—, —C(═O)—, —C(═S)—, —S(═O)—, —S(═O)$_2$— and —N(R)C(═O)N(R)—;
in any one of the above cases, the number of heteroatoms or heteroatom groups is each independently selected from 1, 2 and 3.
In some embodiments of the present disclosure, for the above combination, the compound of formula (II) is selected from one of the following compounds:
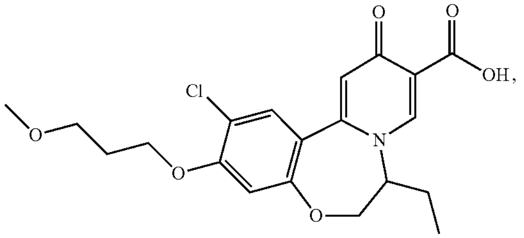
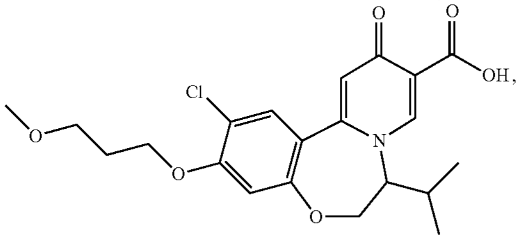
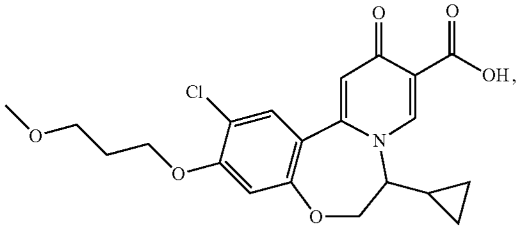
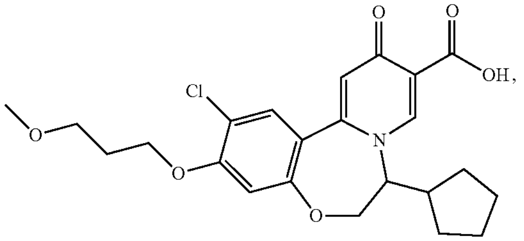
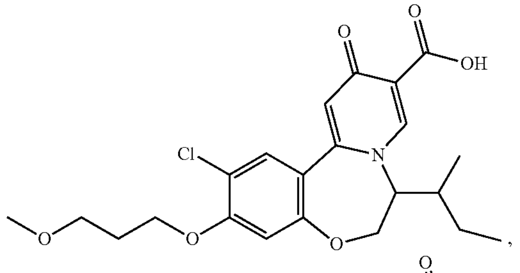
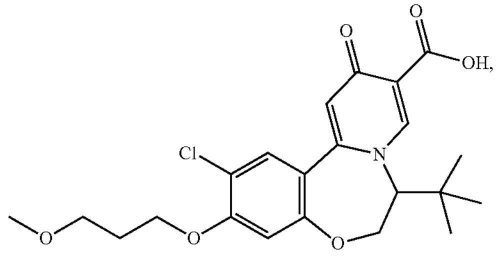
-continued
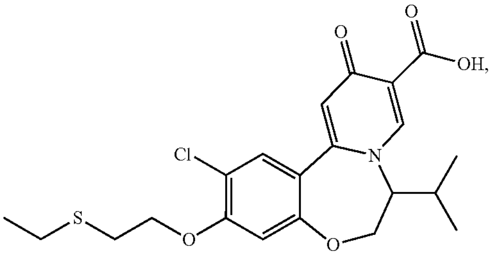
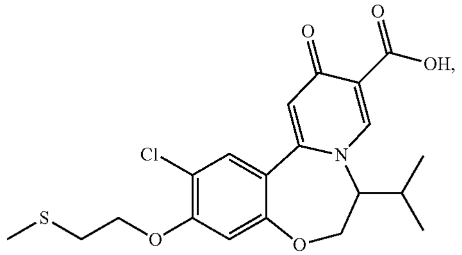
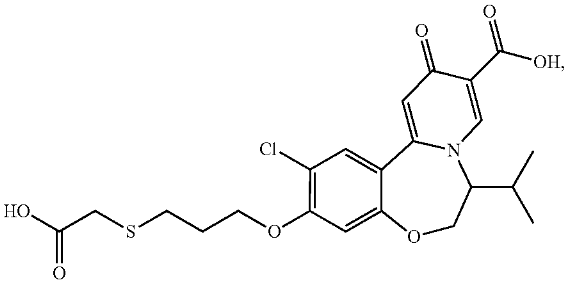
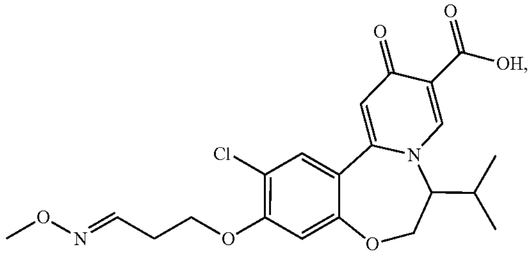
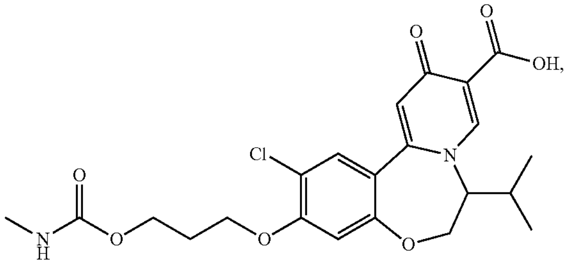
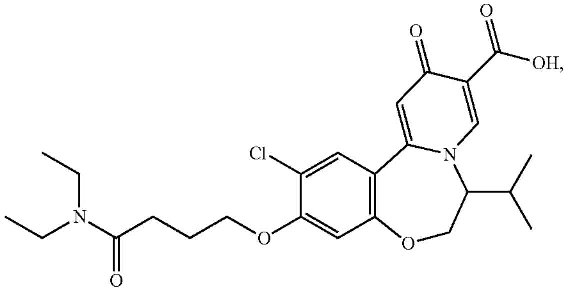

-continued
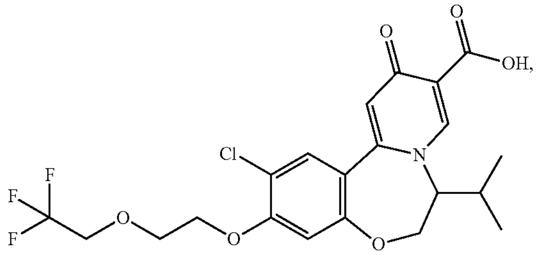
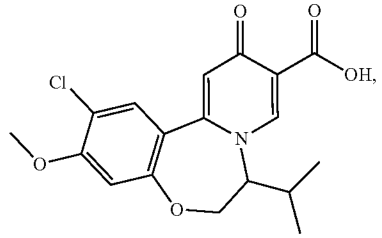
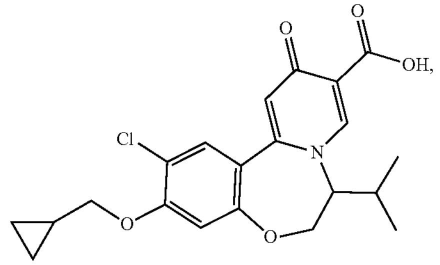
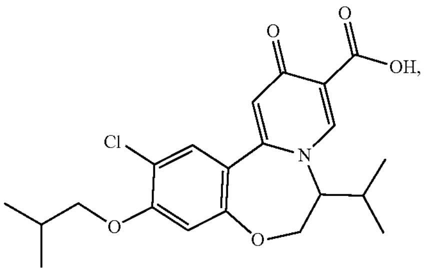
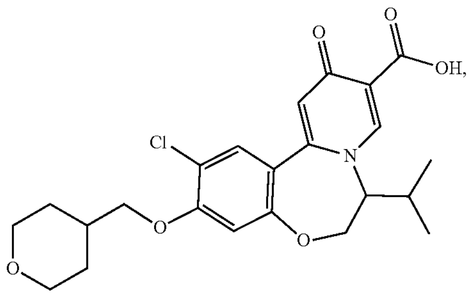
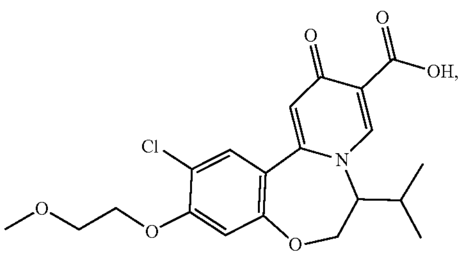
-continued
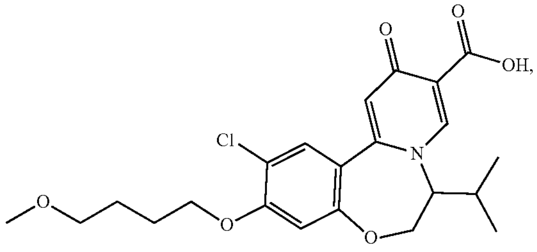
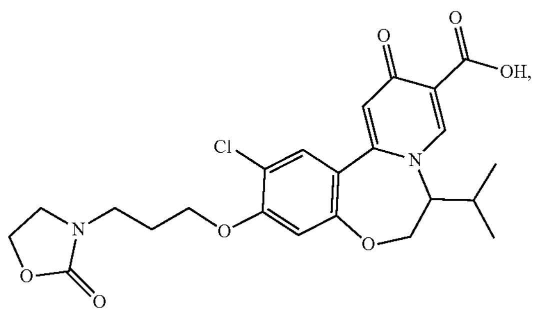
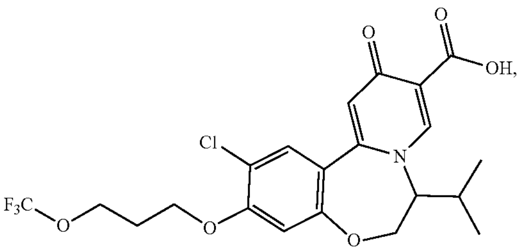
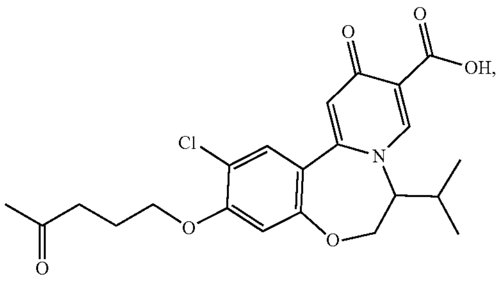
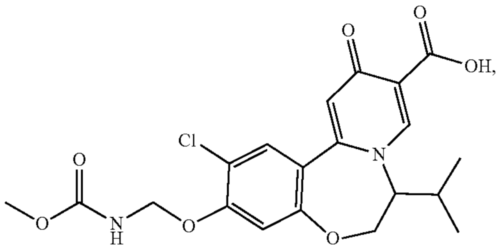
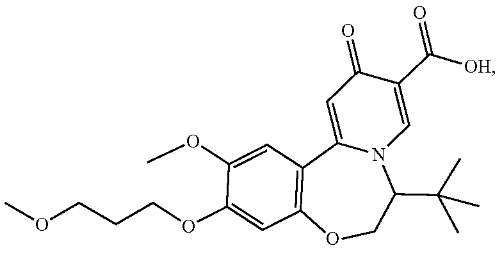

-continued
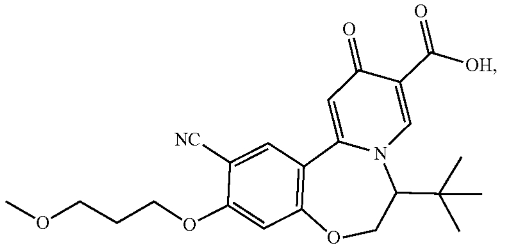
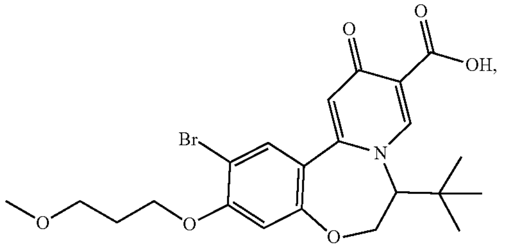
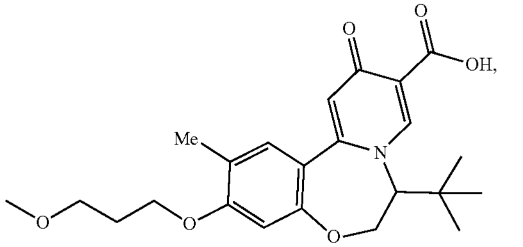
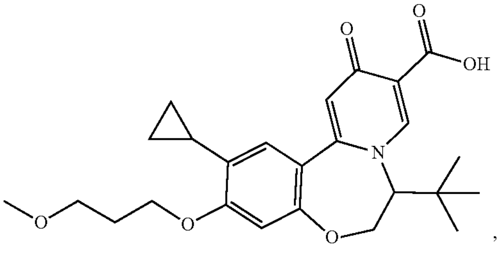
, and
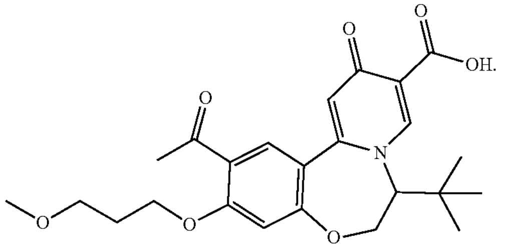
In some embodiments of the present disclosure, for the above combination, the compound of formula (II) is selected from one of the following compounds:
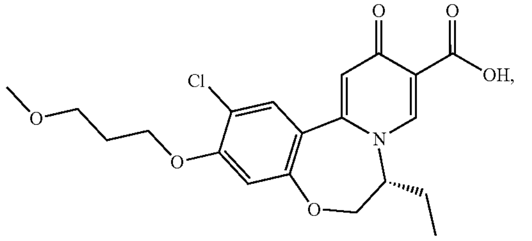
-continued
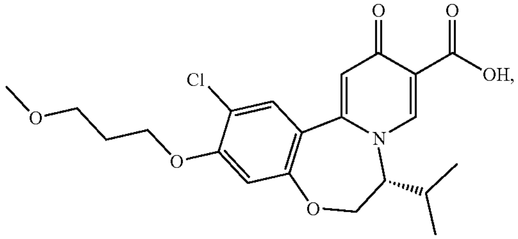
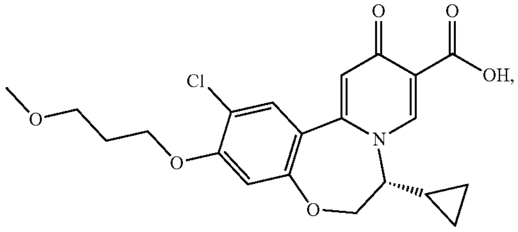
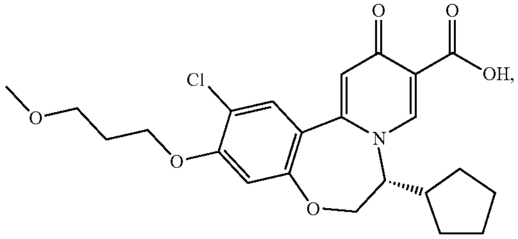
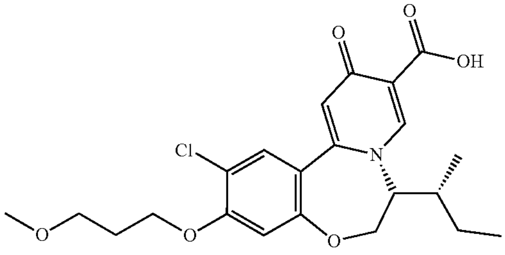
,
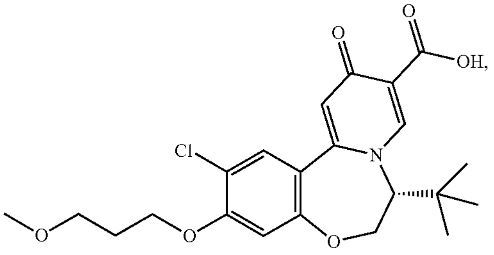
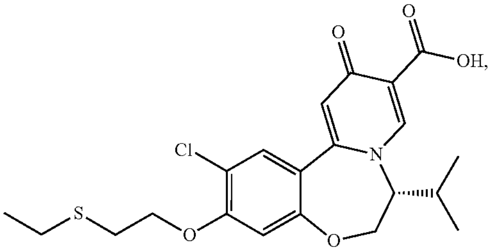
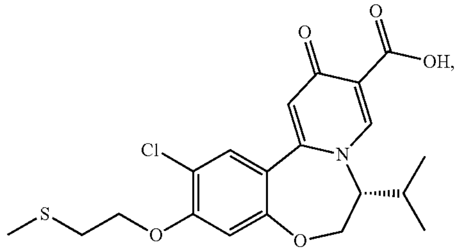

-continued
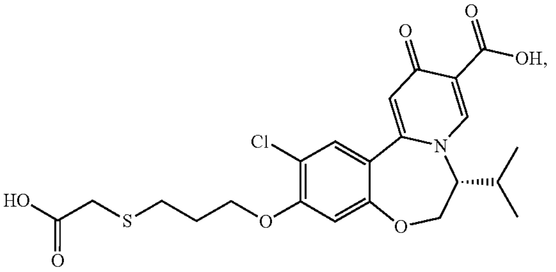
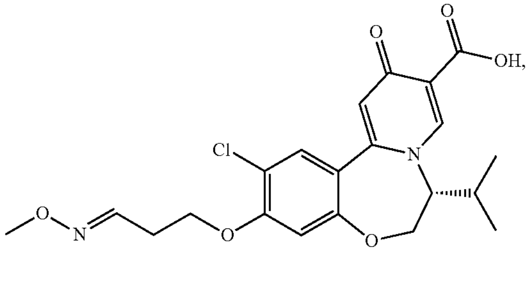
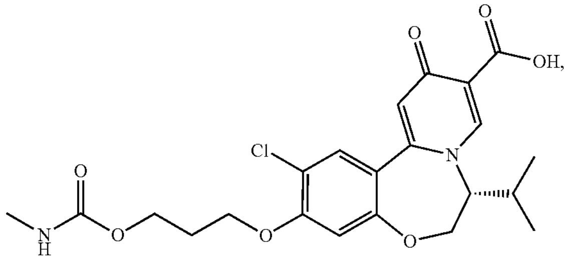
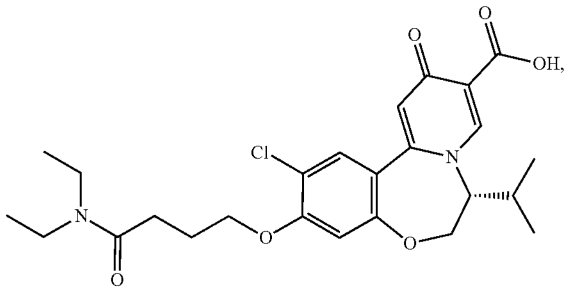
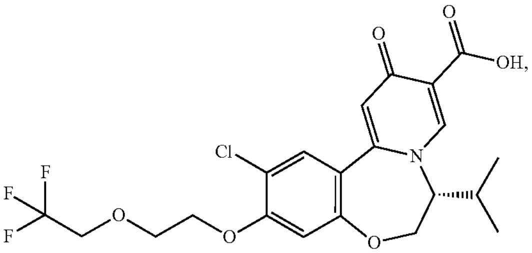
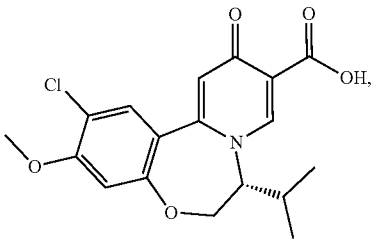
-continued
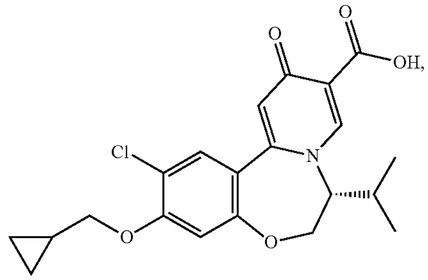
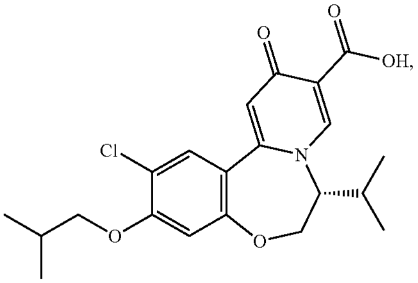
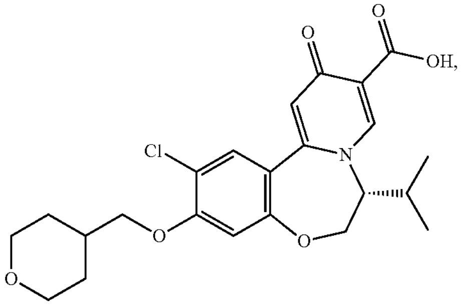
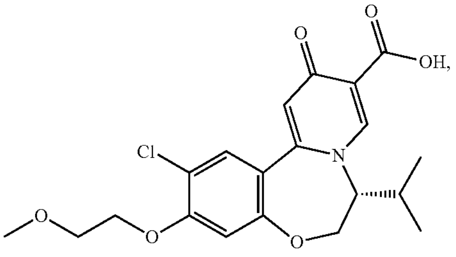
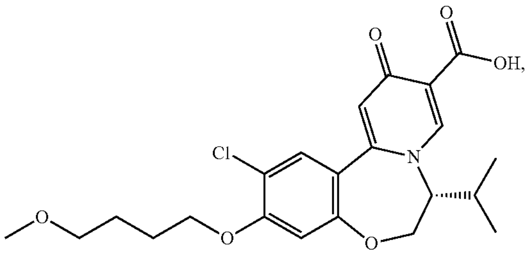
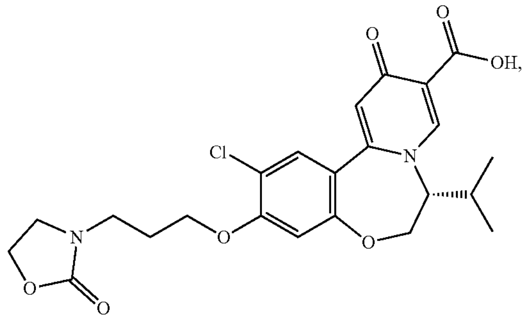

-continued

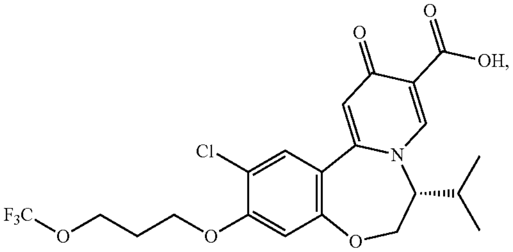

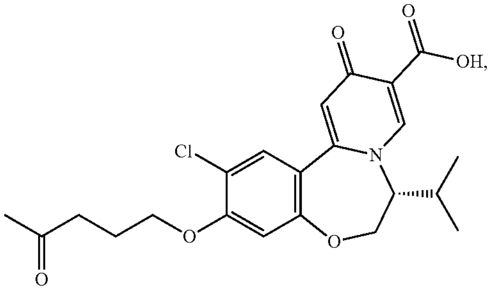

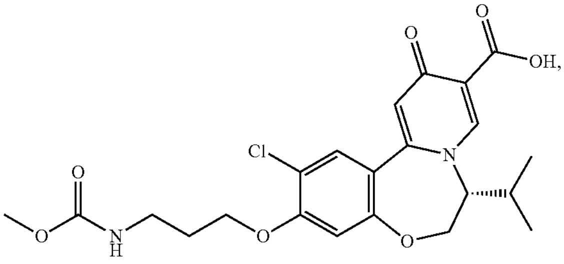

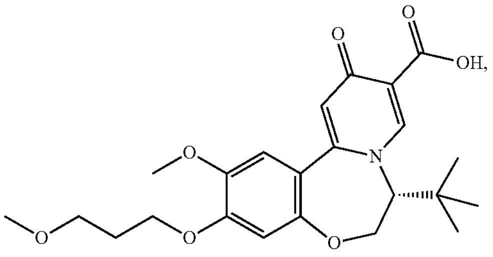

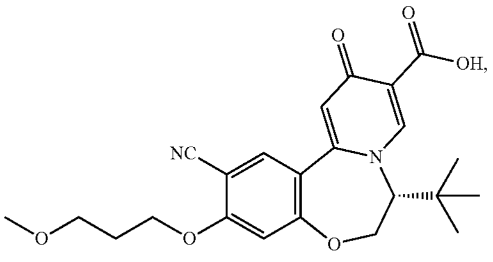

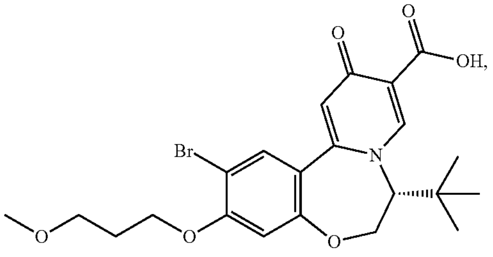

-continued

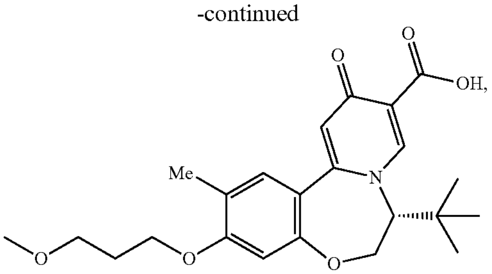

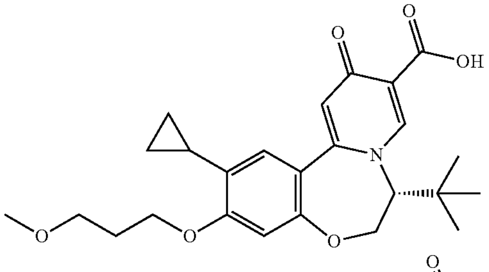

, and

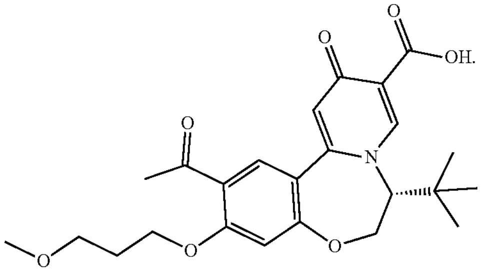

Preferably, the hepatitis B surface antigen inhibitor has a structure shown as the following formula (IIa):

(IIa)

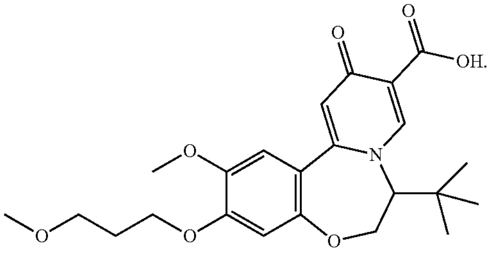

Preferably, the hepatitis B surface antigen inhibitor has a structure shown as the following formula (IIb):

(IIb)

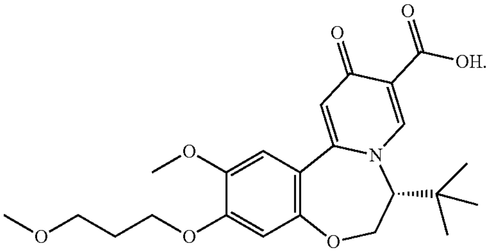

In another embodiment, the hepatitis B surface antigen inhibitor is selected from one of the compounds of formula (III):

(III)

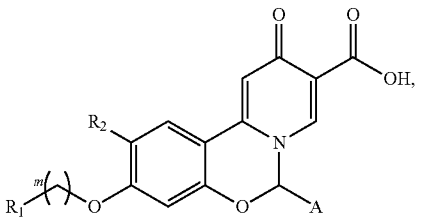

or a pharmaceutically acceptable salt thereof, wherein, $R_1$ is selected from H, OH, CN, $NH_2$, or from the following groups optionally substituted with 1, 2 or 3 R: $C_{1-5}$ alkyl, $C_{1-5}$ heteroalkyl, $C_{2-5}$ alkynyl, $C_{3-6}$ cycloalkyl and 3-6 membered heterocycloalkyl;

$R_2$ is selected from H, halogen, or from the following groups optionally substituted with 1, 2 or 3 R: $C_{1-3}$ alkyl and $C_{1-3}$ heteroalkyl;

m is selected from 0, 1, 2, 3, 4 and 5;

A is selected from the following groups optionally substituted with 1, 2 or 3 R: phenyl and 5-6 membered heteroaryl;

R is selected from H, halogen, OH, CN, $NH_2$, =O, $CH_3$, $CH_3CH_2$, $CH_3O$, $CF_3$, $CHF_2$ and $CH_2F$;

the "hetero" in $C_{1-5}$ heteroalkyl, 3-6 membered heterocycloalkyl, $C_{1-3}$ heteroalkyl and 5-6 membered heteroaryl is each independently selected from: N, —O—, =O, —S—, —NH—, —(C=O)—, —(S=O)— and —$(S=O)_2$—;

in any one of the above cases, the number of heteroatoms or heteroatom groups is each independently selected from 1, 2 and 3.

In some embodiments of the present disclosure, for the above combination, the compound of formula (III) is selected from one of the following compounds:

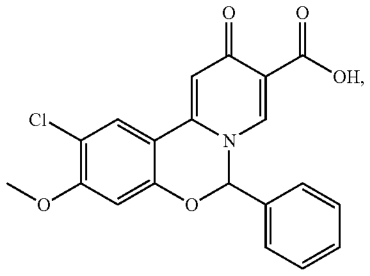

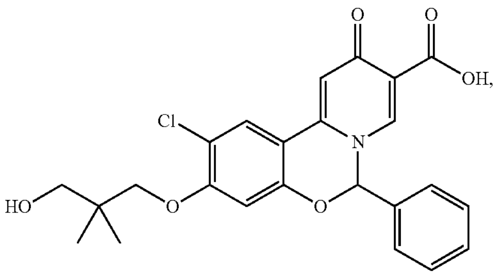

-continued

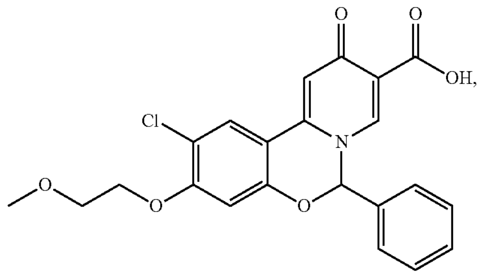

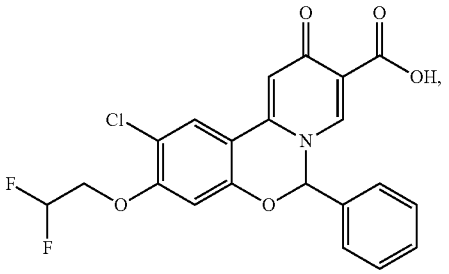

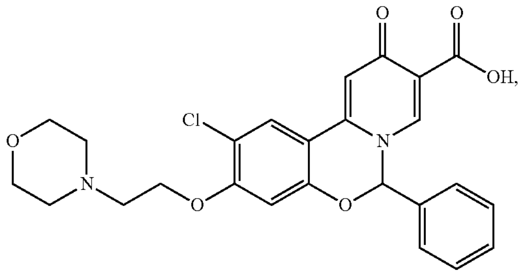

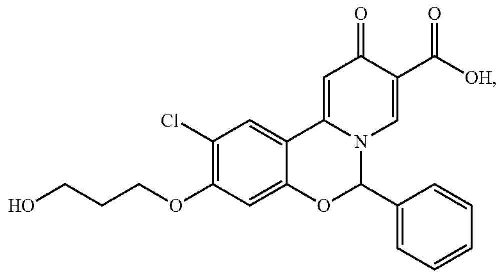

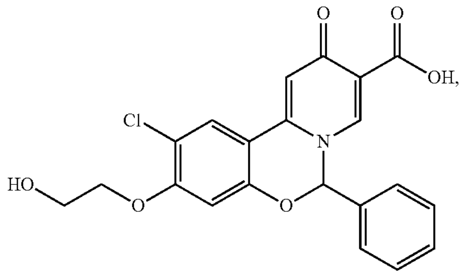

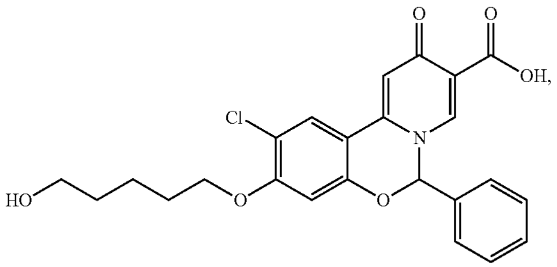

-continued
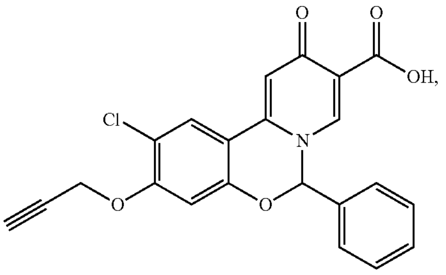
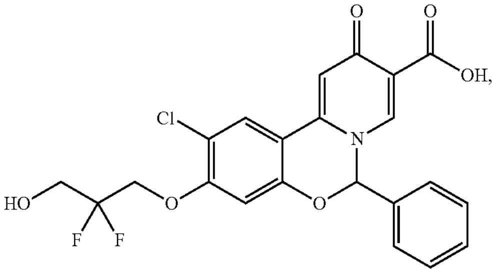
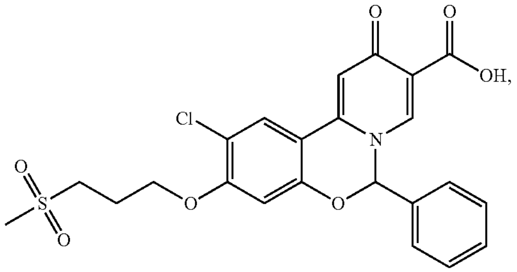
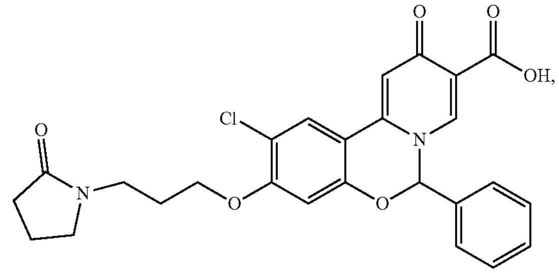
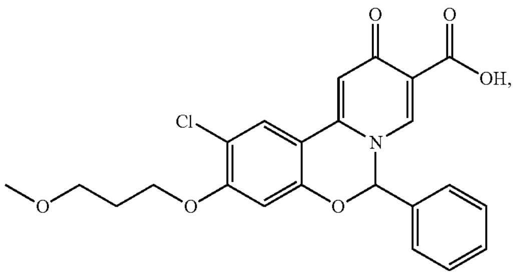
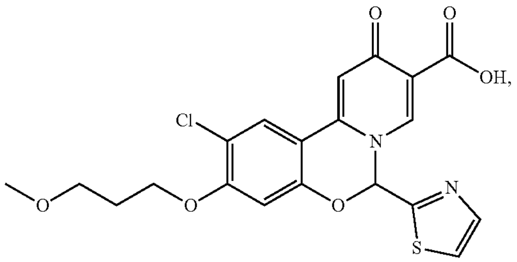
-continued
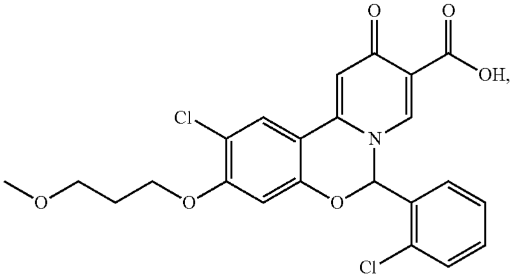
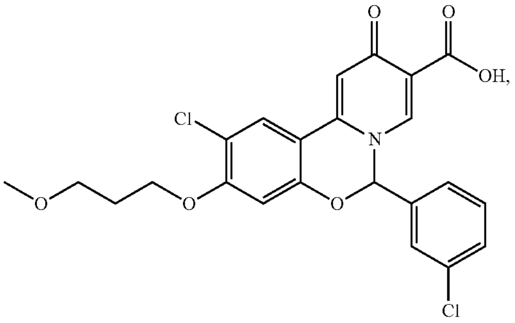
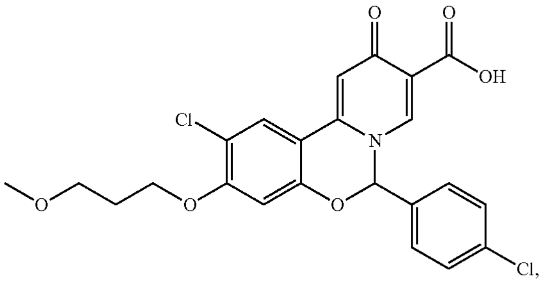
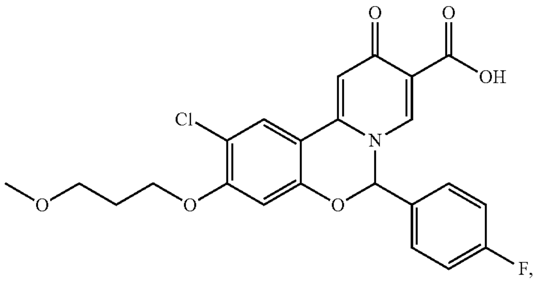
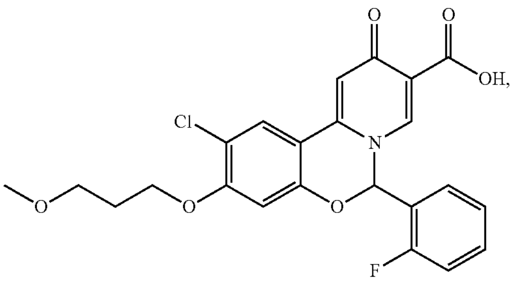

-continued
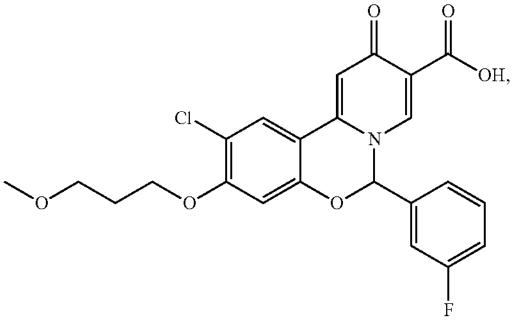
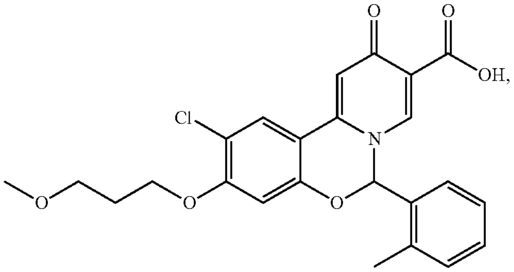
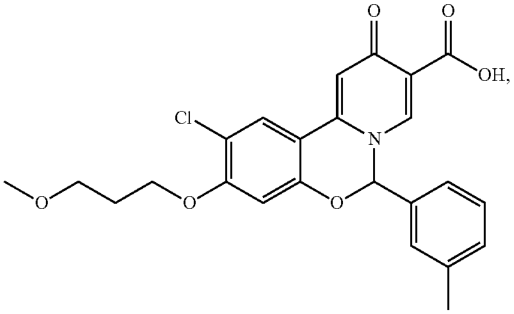
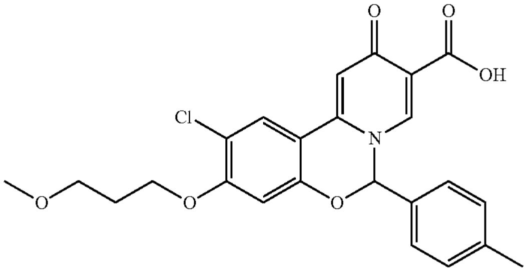
,
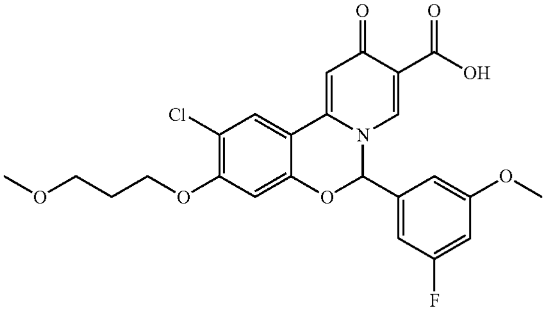
,
-continued
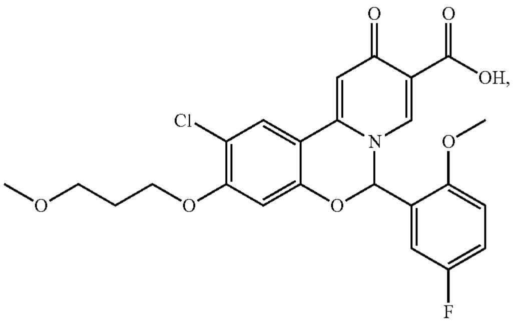
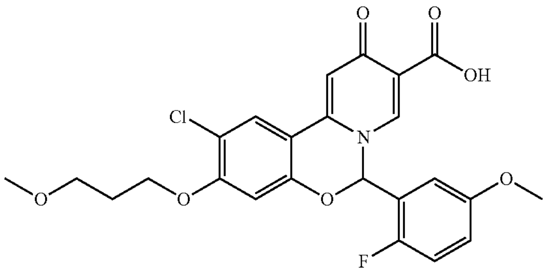
,
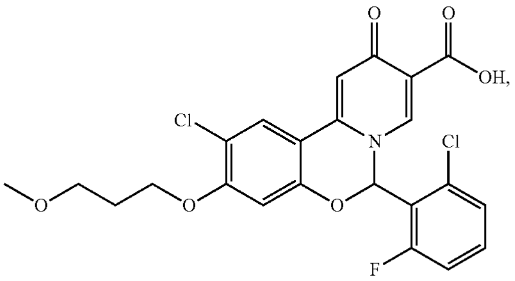
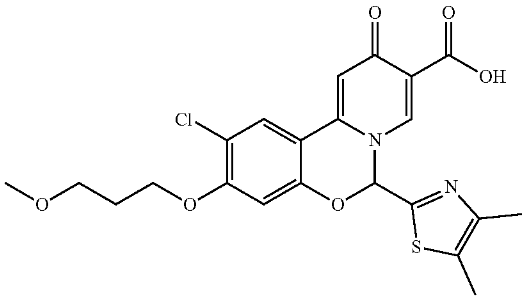
,
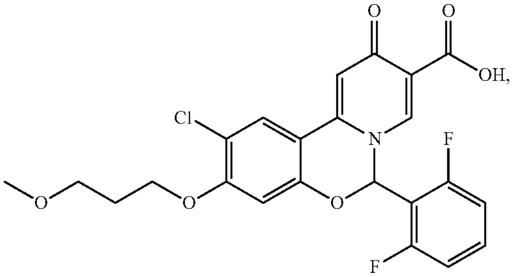

-continued
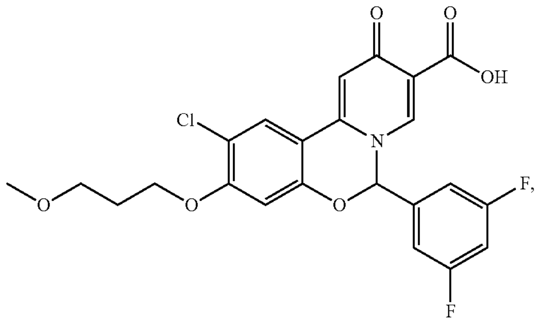
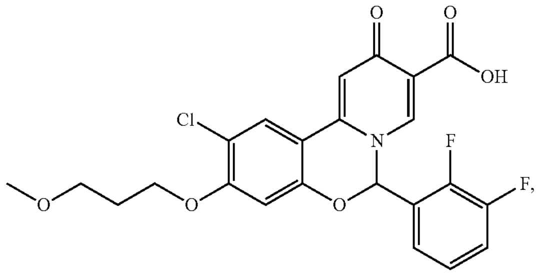
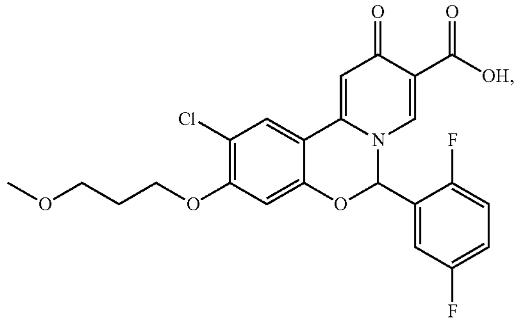
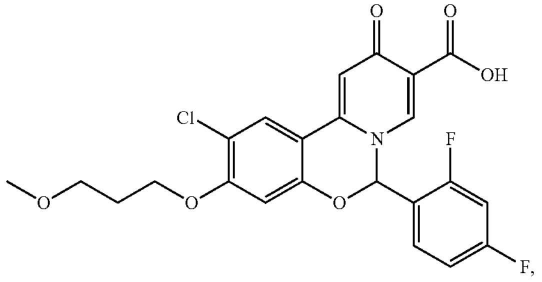
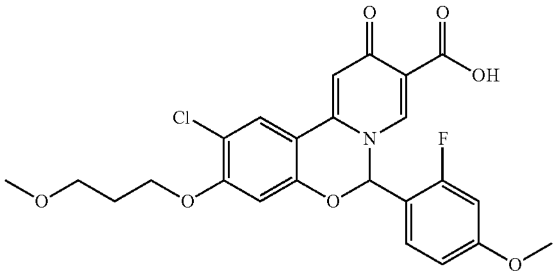
,
-continued
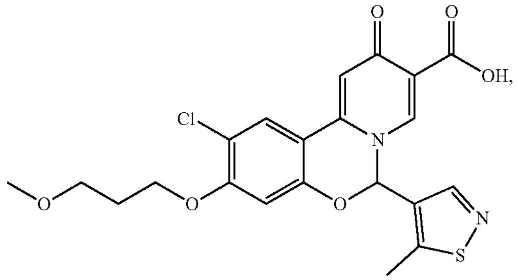
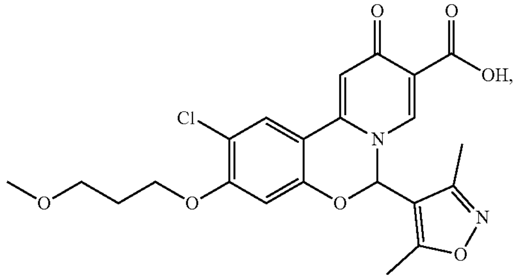
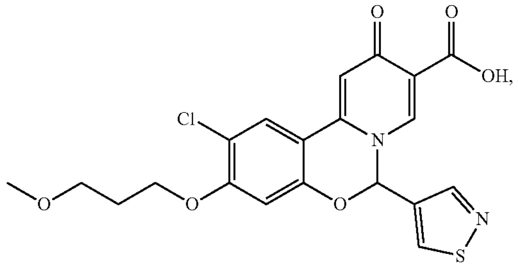
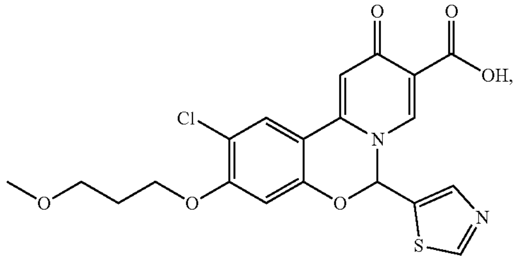
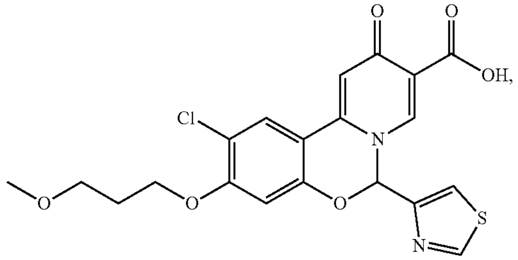
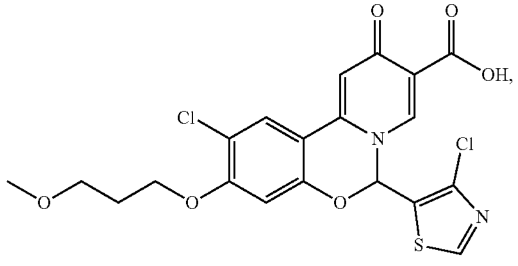

-continued
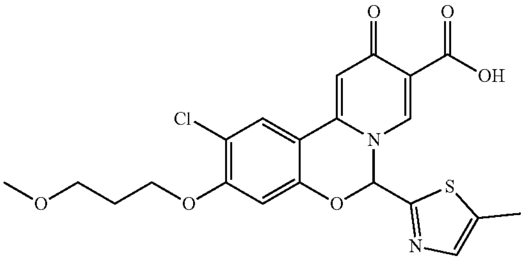
,
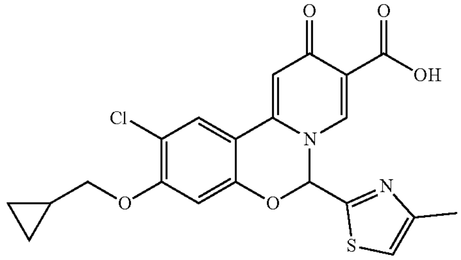
,
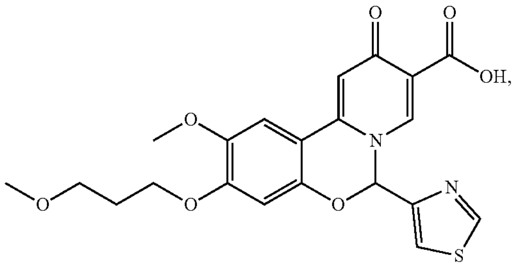
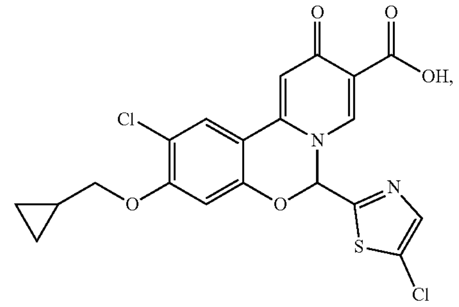
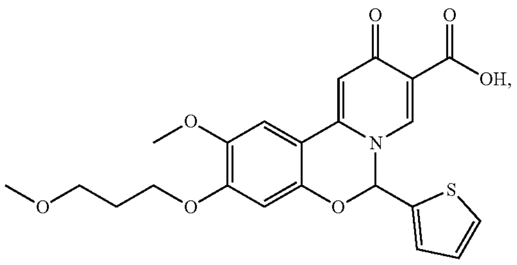
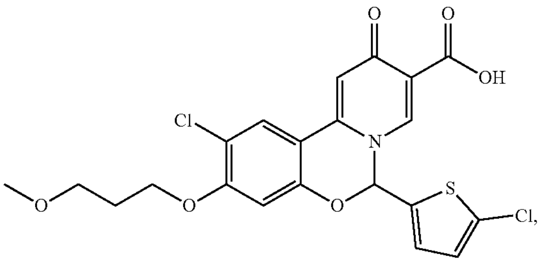
-continued
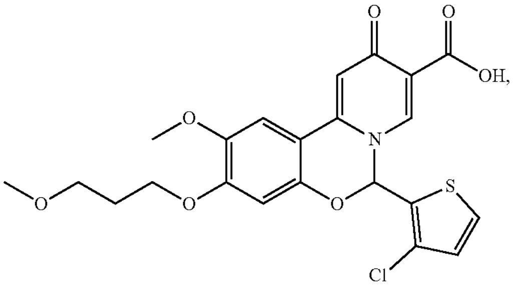
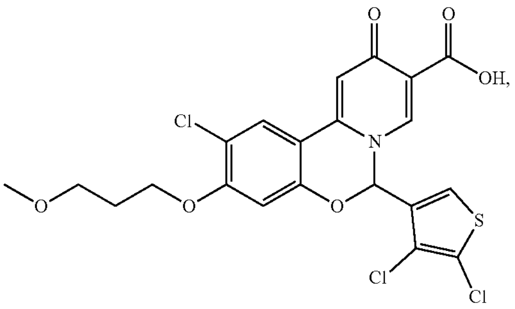
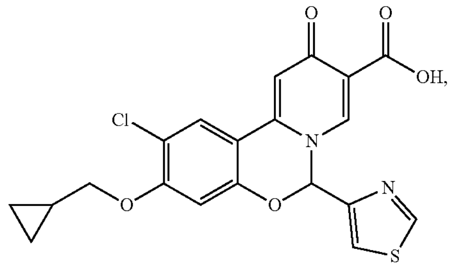
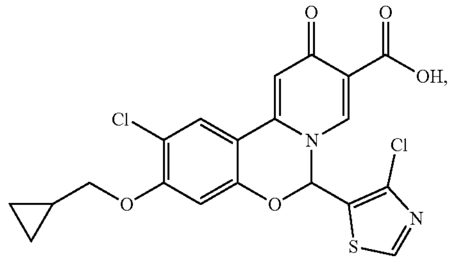
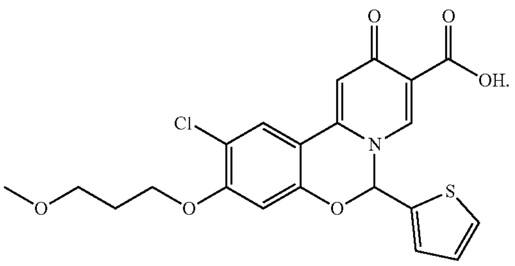
In some embodiments of the present disclosure, for the above combination, the compound of formula (III) is selected from one of the following compounds:

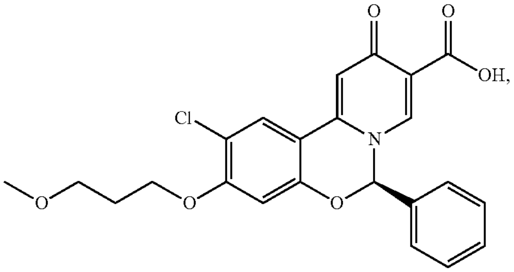
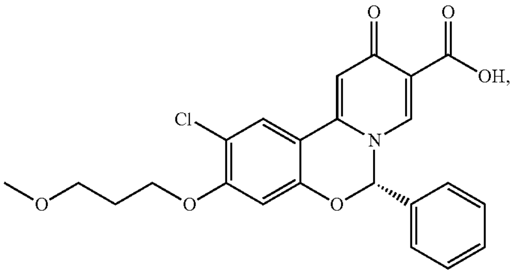
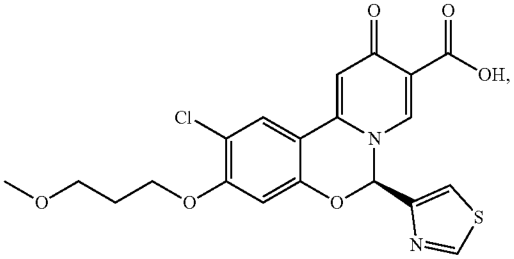
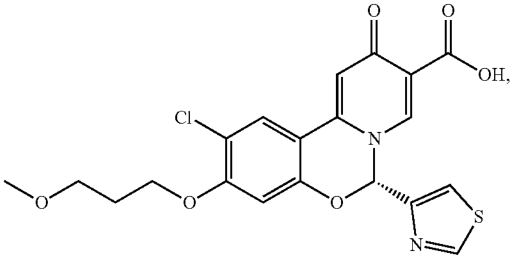
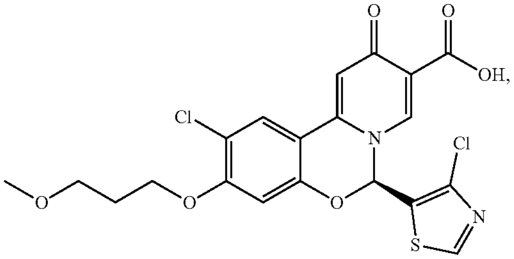
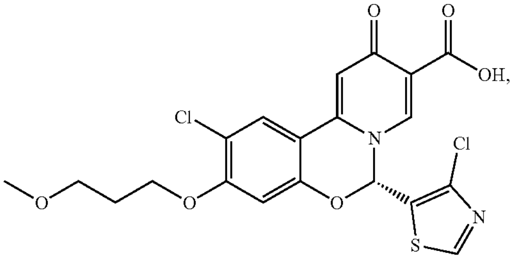
-continued
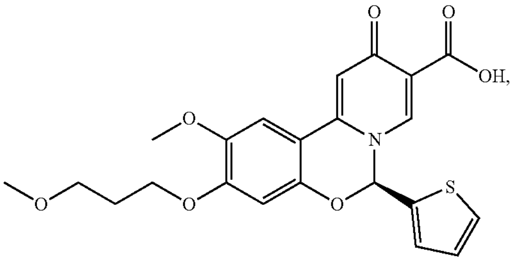
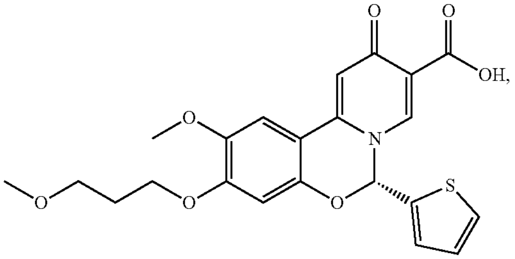
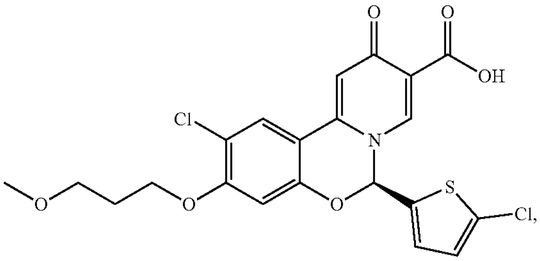
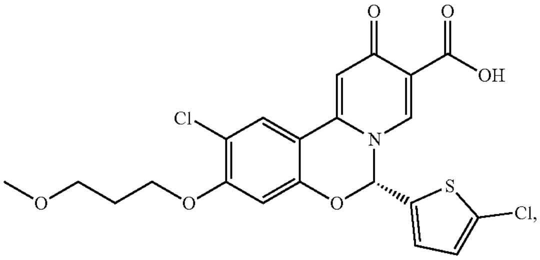
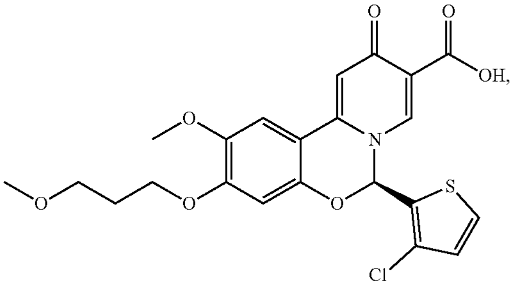
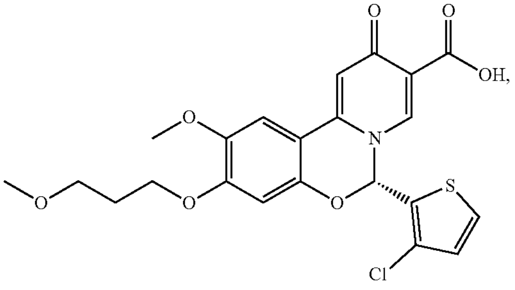

-continued

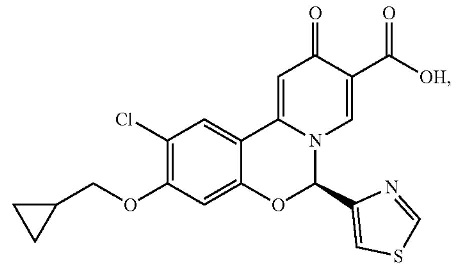

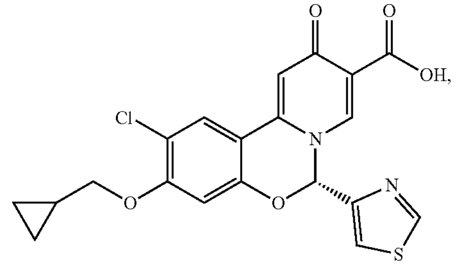

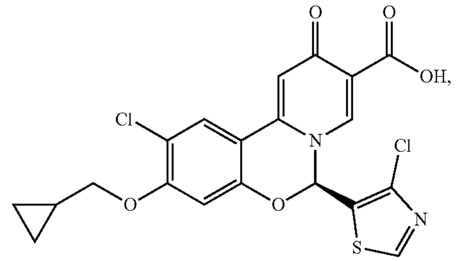

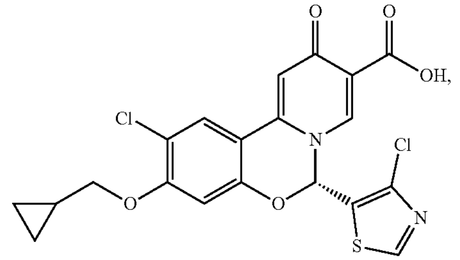

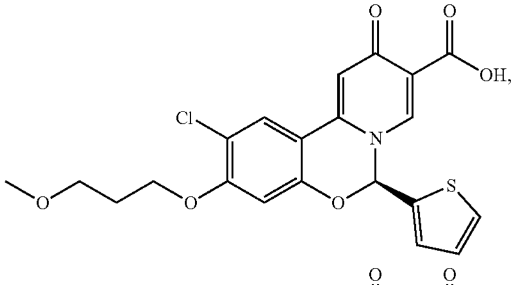

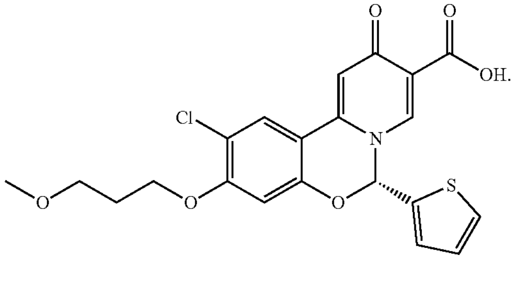

Preferably, the hepatitis B surface antigen inhibitor has a structure shown as the following formula (IIIa):

(IIIa)

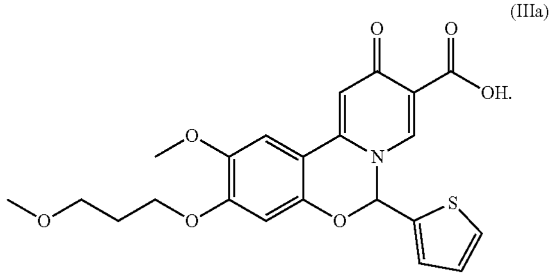 [SMILES: COCCCOc1cc2c(cc1OC)-c1cc(=O)c(C(=O)O)cn1C(c1cccs1)O2]

Preferably, the hepatitis B surface antigen inhibitor has a structure shown as the following formula (IIIb):

(IIIb)

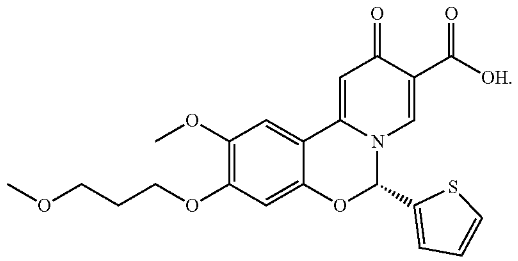

For the combination of the present disclosure, the reverse transcriptase inhibitor is selected from: lamivudine, adefovir dipivoxil, entecavir, tenofovir disoproxil fumarate and tenofovir alafenamide fumarate.

Preferably, wherein, the reverse transcriptase inhibitor is selected from entecavir and tenofovir disoproxil fumarate.

For the combination of the present disclosure, a pharmaceutical composition is prepared by mixing the compound of formula (I) or the pharmaceutically acceptable salt thereof with any one of the groups a to c of drugs as pharmaceutically active ingredients.

Where, the preparation of the pharmaceutical composition by mixing the pharmaceutically active ingredients is that a compound pharmaceutical composition is prepared by mixing two or three different drugs as pharmaceutically active ingredients.

For the combination of the present disclosure, the compound of formula (I) or the pharmaceutically acceptable salt thereof and any one of the groups a to c of drugs, as pharmaceutically active ingredients, are separately prepared into pharmaceutical compositions, and the pharmaceutical compositions are further packaged separately and administered separately at the time of administration.

Where, the separate administrations comprise the administration of one or two of the pharmaceutical compositions, followed by the administration of another one or two of the pharmaceutical compositions, and the administration of two or three of the pharmaceutical compositions simultaneously.

The present disclosure provides use of the combination of the present disclosure in the manufacture of a medicament for treating hepatitis B virus infection.

The pharmaceutical preparation composition of the present disclosure comprises the combination of the present disclosure and at least one pharmaceutically acceptable carrier and/or excipient.

The present disclosure further provides a kit comprising the combination of the present disclosure, or the pharmaceutical preparation composition of the present disclosure.

The present disclosure further provides use of the pharmaceutical composition or the kit in the manufacture of a medicament for treating hepatitis B.

The combination of the present disclosure can be selected as follows, in the manner of separate packaging and separate administration.

Mode of Administration

The following does not limit the mode of administration of the combination of the present disclosure.

The components of the combination of the present disclosure may each be prepared separately, or some or all of them may be co-prepared as a pharmaceutical composition. In some embodiments, the combination of the present disclosure may be prepared as a pharmaceutical composition suitable for single or multiple administration.

The components of the combination of the present disclosure may each be administered separately or some or all of them may be co-administered. The components of the combination of the present disclosure may be not administered substantially simultaneously, or some or all of them may be administered substantially simultaneously. The components of the combination of the present disclosure may have the same or different administration periods.

The components of the combination of the present disclosure may each independently be administered by any suitable route, including, but not limited to, orally or parenterally (by intravenous, intramuscular, subcutaneous, intraperitoneal, spinal or other parenteral routes of administration, for example by injection or infusion). In some embodiments, the components of the combination of the present disclosure may each be administered independently orally or by injection, for example intravenously or intraperitoneally.

The components of the combination of the present disclosure may each independently be in a suitable dosage form including, but not limited to, tablets, buccal tablets, pills, capsules (e.g., hard capsules, soft capsules, enteric coated capsules, microcapsules), elixirs, granules, syrups, injections (intramuscular, intravenous, intraperitoneal), granules, emulsions, suspensions, solutions, dispersions and sustained release preparations for oral or non-oral administration.

The components of the combination of the present disclosure may each independently comprise a pharmaceutically acceptable carrier and/or excipient.

Technical Effects

The compound of formula (I) is a hepatitis B core protein inhibitor, and can interfere a virus cccDNA library and inhibit HBV virus replication; the compounds of formula (II) and formula (III) are hepatitis B surface antigen inhibitors, can effectively reduce HBsAg. The replication process of HBV virus can be inhibited in a multi-channel manner by using the compound of formula (I) and the hepatitis B surface antigen inhibitors in a combined manner, or using the compound of formula (I) and nucleoside or nucleotide reverse transcriptase inhibitors in a combined manner, or using the drugs of the three mechanisms in a combined manner, and the purposes of improving the curative effect, reducing the toxic and side effects, shortening the administration treatment period and dosage, reducing the drug resistance and the like can be achieved under the multi-channel conditions, thereby achieving the effects of reducing the HBV loading and reducing and even eliminating the HBsAg.

Definitions and Description

Unless otherwise indicated, the following terms when used in the descriptions and the claims of the present disclosure have the following meanings. A specific term or phrase should not be considered indefinite or unclear in the absence of a particular definition, but should be understood in the ordinary sense. When a trade name appears herein, it is intended to refer to its corresponding commodity or active ingredient thereof.

The term "pharmaceutically acceptable" is used herein in terms of those compounds, materials, compositions, and/or dosage forms, which are suitable for use in contact with human and animal tissues within the scope of reliable medical judgment, with no excessive toxicity, irritation, allergic reaction or other problems or complications, commensurate with a reasonable benefit/risk ratio.

The term "pharmaceutically acceptable salt" refers to a salt of the compound of the present disclosure that is prepared by reacting the compound having a specific substituent of the present disclosure with a relatively non-toxic acid or base. When the compound of the present disclosure contains a relatively acidic functional group, a base addition salt can be obtained by bringing the compound into contact with a sufficient amount of base in a pure solution or a suitable inert solvent. The pharmaceutically acceptable base addition salt includes a salt of sodium, potassium, calcium, ammonium, organic amine or magnesium or similar salts. When the compound of the present disclosure contains a relatively basic functional group, an acid addition salt can be obtained by bringing the compound into contact with a sufficient amount of acid in a pure solution or a suitable inert solvent. Examples of the pharmaceutically acceptable acid addition salt include an inorganic acid salt, wherein the inorganic acid includes, for example, hydrochloric acid, hydrobromic acid, nitric acid, carbonic acid, bicarbonate, phosphoric acid, monohydrogen phosphate, dihydrogen phosphate, sulfuric acid, hydrogen sulfate, hydroiodic acid, phosphorous acid, and the like; and an organic acid salt, wherein the organic acid includes, for example, acetic acid, propionic acid, isobutyric acid, maleic acid, malonic acid, benzoic acid, succinic acid, suberic acid, fumaric acid, lactic acid, mandelic acid, phthalic acid, benzenesulfonic acid, p-toluenesulfonic acid, citric acid, tartaric acid, and methanesulfonic acid, and the like; and an salt of amino acid (such as arginine and the like), and a salt of an organic acid such as glucuronic acid and the like. Certain specific compounds of the present disclosure that contain both basic and acidic functional groups can be converted to any base or acid addition salt.

The pharmaceutically acceptable salt of the present disclosure can be prepared from the parent compound that contains an acidic or basic moiety by conventional chemical method. Generally, such salt can be prepared by reacting the free acid or base form of the compound with a stoichiometric amount of an appropriate base or acid in water or an organic solvent or a mixture thereof.

The term "pharmaceutical composition" refers to a mixture of one or more active ingredients of the present disclosure or a pharmaceutical combination thereof and a pharmaceutically acceptable excipient. The purpose of the pharmaceutical composition is to facilitate administration of the compounds of the present disclosure or pharmaceutical combinations thereof to a subject.

The term "pharmaceutically acceptable carrier" refers to any preparation or carrier medium capable of delivering an effective amount of an active substance of the present disclosure, without interfering with the biological activity of the active substance and without toxic and side effects to the host or patient, representative carriers including water, oils, vegetables and minerals, cream bases, lotion matrices, ointment matrices, and the like. Such matrices include suspending agents, viscosity increasing agents, skin penetration enhancers, and the like. Their preparations are known to those skilled in the cosmetic or topical pharmaceutical field.

The term "excipient" generally refers to a carrier, diluent and/or medium necessary to prepare an effective pharmaceutical composition.

The word "include" or "comprise" should be understood in an open and non-exclusive sense, i.e., "including, but not limited to".

The term "treating" or "treatment" refers to administering the compound or preparation described herein to prevent, ameliorate, or eliminate a disease or one or more symptoms associated with the disease, and includes:

(1) preventing the occurrence of a disease or a disease condition in a mammal, particularly when such mammal is predisposed to the disease condition but has not yet been diagnosed as having it;

(2) inhibiting a disease or a disease condition, i.e., arresting its development; and (3) alleviating a disease or a disease condition, i.e., causing regression of the disease or the disease condition.

The term "effective amount" or "therapeutically effective amount" with respect to a drug or pharmacologically active agent refers to a sufficient amount of a drug or agent that is not toxic but yet achieves the desired effect. For oral dosage forms of the present disclosure, an "effective amount" of one active substance in the composition is the amount required to achieve the desired effect when combined with another active substance in the composition. The determination of an effective amount varies from person to person, depending on the age and general condition of the recipient and also on the particular active substance, and an appropriate effective amount in a case may be determined by those skilled in the art in the light of routine tests.

The term "administering" or "administration" refers to physically introducing a composition comprising a therapeutic agent to a subject using any one of a variety of methods and delivery systems known to those skilled in the art. Routes of administration include intravenous, intramuscular, subcutaneous, intraperitoneal, spinal or other parenteral routes of administration, for example by injection or infusion. The phrase "parenteral administration" as used herein refers to modes of administration other than enteral and topical administration, typically by injection, and includes, but is not limited to, intravenous, intramuscular, intraarterial, intrathecal, intralymphatic, intralesional, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion, and in vivo electroporation. In certain embodiments, the combination is administered by a non-parenteral route, and in certain embodiments, the combination is administered orally. Other non-parenteral routes include topical, epidermal or mucosal routes of administration, for example, intranasally, vaginally, rectally, sublingually or topically. Administration may also be performed, e.g., once, multiple times, and/or over one or more extended periods of time.

The term "subject" is a mammal. In some embodiments, the subject is a mouse. In some embodiments, the subject is a human.

As used herein, "combination" or "combination use" means that two or more active substances may be administered to a subject simultaneously as single preparations, or administered sequentially in any order as single preparations.

The term "active ingredient", "therapeutic agent", "active substance" or "active agent" refers to a chemical entity that is effective in treating a target disorder, disease or condition.

The compound of the present disclosure may have a specific geometric or stereoisomeric form. The present disclosure contemplates all such compounds, including cis and trans isomer, (−)- and (+)-enantiomer, (R)- and (S)-enantiomer, diastereoisomer, (D)-isomer, (L)-isomer, and racemic mixture and other mixtures, for example, an enantiomer or diastereoisomer enriched mixture, all of which are encompassed within the scope of the present disclosure. The substituent such as alkyl may have an additional asymmetric carbon atom. All these isomers and mixtures thereof are encompassed within the scope of the present disclosure.

Unless otherwise specified, the term "enantiomer" or "optical isomer" refers to stereoisomers that are mirror images of each other.

Unless otherwise specified, the term "cis-trans isomer" or "geometric isomer" is caused by the inability of a double bond or a single bond of carbon atoms on the ring to freely rotate.

Unless otherwise specified, the term "diastereomer" refers to stereoisomers in which the molecules have two or more chiral centers and are not mirror images of each other.

Unless otherwise specified, "(+)" refers to dextrorotation, "(−)" refers to levorotation, "(±)" refers to racemization.

Unless otherwise specified, the absolute configuration of a stereogenic center is represented by a wedged solid bond ( ) and a wedged dashed bond ( ), and the relative configuration of a stereogenic center is represented by a straight solid bond ( ) and a straight dashed bond ( ). A wave line ( ) represents a wedged solid bond ( ) or a wedged dashed bond ( ), or represents a straight solid bond ( ) or a straight dashed bond ( ).

The term "substituted" means one or more than one hydrogen atom(s) on a specific atom are substituted with the substituent, including deuterium and hydrogen variants, as long as the valence of the specific atom is normal and the substituted compound is stable. When the substituent is an oxygen (i.e., =O), it means two hydrogen atoms are substituted. Positions on an aromatic ring cannot be substituted with a ketone. The term "optionally substituted" means an atom can be substituted with a substituent or not, unless otherwise specified, the type and number of the substituent may be arbitrary as long as being chemically achievable.

When any variable (such as R) occurs in the constitution or structure of the compound more than once, the definition of the variable at each occurrence is independent. Thus, for example, if a group is substituted with 0-2 R, the group can be optionally substituted with up to two R, wherein the definition of R at each occurrence is independent. Moreover, a combination of the substituent and/or the variant thereof is allowed only when the combination results in a stable compound.

When the number of a linking group is 0, such as $-(CRR)_0-$, it means that the linking group is a single bond.

When one of the variables is selected from a single bond, it means that the two groups linked by the single bond are connected directly. For example, when L in A-L-Z represents a single bond, the structure of A-L-Z is actually A-Z.

When a substituent is vacant, it means that the substituent does not exist. For example, when X is vacant in A-X, the structure of A-X is actually A. When the enumerative substituent does not indicate by which atom it is linked to the group to be substituted, such substituent can be bonded by any atom thereof. For example, when pyridyl acts as a substituent, it can be linked to the group to be substituted by any carbon atom on the pyridine ring.

When the enumerative linking group does not indicate the direction for linking, the direction for linking is arbitrary, for example, the linking group L contained in

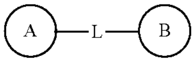

is -MW-, then -MW- can link ring A and ring B to form

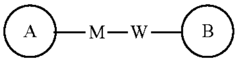

in the direction same as left-to-right reading order, and form

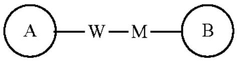

in the direction contrary to left-to-right reading order. A combination of substituents and/or variants thereof is allowed only when such combination can result in a stable compound.

Unless otherwise specified, when a group has one or more connectable sites, any one or more of the sites of the group may be connected to other groups by chemical bonds. When there is no designated connecting mode for a chemical bond and H atoms are present at a connectable site, the number of the H atoms at the connectable site is correspondingly reduced based on the number of the connected chemical bonds, and a group with a corresponding valence number is thus formed. The chemical bond that connects the site to another group may be represented by a straight solid bond (), a straight dashed line bond (), or a wavy line (

). For example, the straight solid bond in $-OCH_3$ refers to being connected to another group via the oxygen atom in the group; the straight dashed bond in

refers to being connected to another group via two ends of the nitrogen atom in the group; the wavy line in

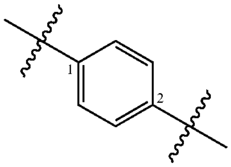 [SMILES: *c1ccc(*)cc1]

refers to being connected to another group via the carbon atoms at positions 1 and 2 in the phenyl group;

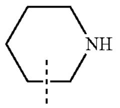

means that any connectable site on the piperidinyl can be connected to another group via 1 chemical bond, and at least 4 connecting modes

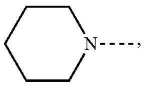, 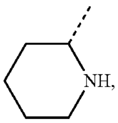, 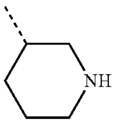 and

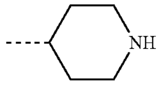

are possible; even if —N— is connected to an H atom,

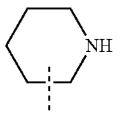

includes the connecting mode of

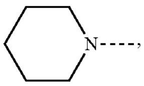, except that when 1 chemical bond is connected to a site, the number of H at that site is correspondingly reduced by 1 and a monovalent piperidinyl is thus formed.

Unless otherwise specified, the number of atoms in a ring is generally defined as the member number of the ring. For example, "5-7 membered ring" refers to a "ring" in which 5 to 7 atoms are arranged in a circle.

Unless otherwise specified, the term "$C_{1-3}$ alkyl" refers to a linear or branched saturated hydrocarbon group consisting of 1 to 3 carbon atoms. The $C_{1-3}$ alkyl includes, but is not limited to, $C_{1-2}$ and $C_{2-3}$ alkyl and the like, and may be monovalent (e.g., methyl), divalent (e.g., methylene), or polyvalent (e.g., methenyl). Examples of $C_{1-3}$ alkyl include, but are not limited to, methyl (Me), ethyl (Et), propyl (including n-propyl and isopropyl), etc. Unless otherwise specified, "$C_{2-8}$ alkenyl" is used to denote a linear or branched hydrocarbon group containing 2 to 8 carbon atoms and at least one carbon-carbon double bond which may be located anywhere in the group.

Unless otherwise specified, the term "4-6 membered heterocycloalkyl", by itself or in combination with other terms, refers to a saturated cyclic group consisting of 4 to 6 ring atoms, of which 1, 2, 3, or 4 ring atoms are heteroatoms independently selected from the group consisting of O, S and N, with the remaining being carbon atoms. The nitrogen atom is optionally quaternized, and the nitrogen and sulfur heteroatoms can be optionally oxidized (i.e., NO and $S(O)_p$, where p is 1 or 2). This includes monocyclic and bicyclic systems, wherein the bicyclic system includes spirocyclic, fused, and bridged rings. Furthermore, with respect to the "4-6 membered heterocycloalkyl", a heteroatom may occupy the position where the heterocycloalkyl is linked to the rest of the molecule. The 4-6 membered heterocycloalkyl includes 5-6 membered, 4 membered, 5 membered, 6 membered heterocycloalkyl, and the like. Examples of 4-6 membered heterocycloalkyl include, but are not limited to, azetidinyl, oxetanyl, thietanyl, pyrrolidinyl, pyrazolidinyl, imidazolidinyl, tetrahydrothienyl (including tetrahydrothien-2-yl, tetrahydrothien-3-yl, etc.), tetrahydrofuryl (including tetrahydrofuran-2-yl, etc.), tetrahydropyranyl, piperidinyl (including 1-piperidinyl, 2-piperidinyl, 3-piperidinyl, etc.), piperazinyl (including 1-piperazinyl, 2-piperazinyl, etc.), morpholinyl (including 3-morpholinyl, 4-morpholinyl, etc.), dioxanyl, dithianyl, isoxazolidinyl, isothiazolidinyl, 1,2-oxazinyl, 1,2-thiazinyl, hexahydropyridazinyl, homopiperazinyl, homopiperidinyl, etc.

Unless otherwise stated, the following terms and phrases used herein are intended to have the following meanings. A particular phrase or term, unless otherwise specifically defined, should not be considered as uncertain or unclear, but construed according to its common meaning. When referring to a trade name, it is intended to refer to its corresponding commercial product or its active ingredient.

The intermediate compounds of the present disclosure can be prepared by a variety of synthetic methods well known to those skilled in the art, including the specific embodiments listed below, embodiments formed by combinations thereof with other chemical synthetic methods, and equivalent substitutions thereof known to those skilled in the art. Preferred embodiments include, but are not limited to, the examples of the present disclosure.

The chemical reactions of the specific embodiments of the present disclosure are carried out in a suitable solvent that must be suitable for the chemical changes in the present disclosure and the reagents and materials required. In order to obtain the compounds of the present disclosure, it is sometimes necessary for those skilled in the art to modify or select a synthesis procedure or a reaction scheme based on the existing embodiments.

The present disclosure is described in detail below by way of examples, which are not intended to limit the present disclosure in any way.

All solvents used in the present disclosure are commercially available and can be used without further purification.

The solvent used in the present disclosure can be commercially available. The present disclosure employs the following abbreviations: EtOH represents ethanol; MeOH represents methanol; TFA represents trifluoroacetic acid; TsOH represents p-toluenesulfonic acid; mp represents melting point; $EtSO_3H$ represents ethanesulfonic acid; $MeSO_3H$ represents methanesulfonic acid; THF represents tetrahydrofuran; EtOAc represents ethyl acetate; THF represents tetrahydrofuran; EA represents ethyl acetate; DMAP represents 4-dimethylaminopyridine; DCM represents dichloromethane; DIPEA represents N,N-diisopropylethylamine.

DETAILED DESCRIPTION OF THE PREFERRED EMBODIMENT

Figure 1:
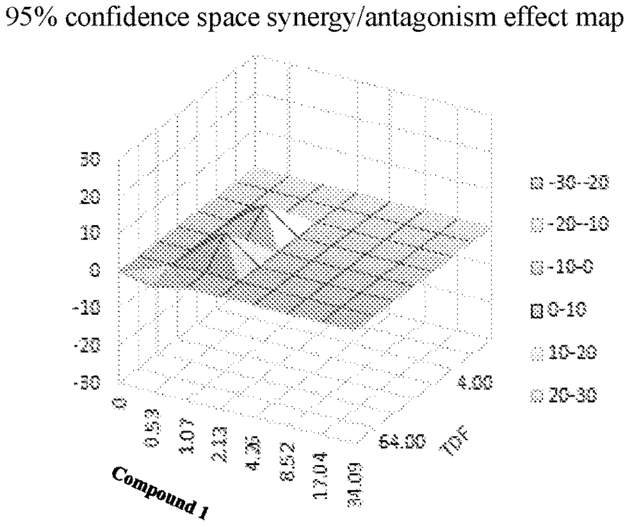
FIG. 1: in vitro combination efficacy profile of compound 1 and TDF.

The present disclosure is described in detail below by way of examples. However, this is by no means disadvantageously limiting the scope of the present disclosure. Although the present disclosure has been described in detail herein and specific examples have also been disclosed, it will be apparent to those skilled in the art that various changes and modifications can be made to the specific examples without departing from the spirit and scope of the present disclosure.

Example 1 Preparation of the Compound 1

1

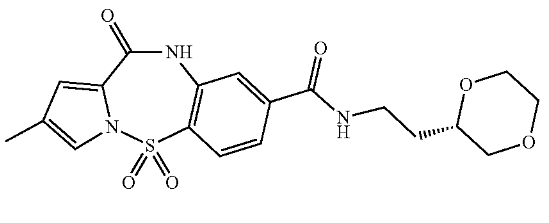

Synthetic Route
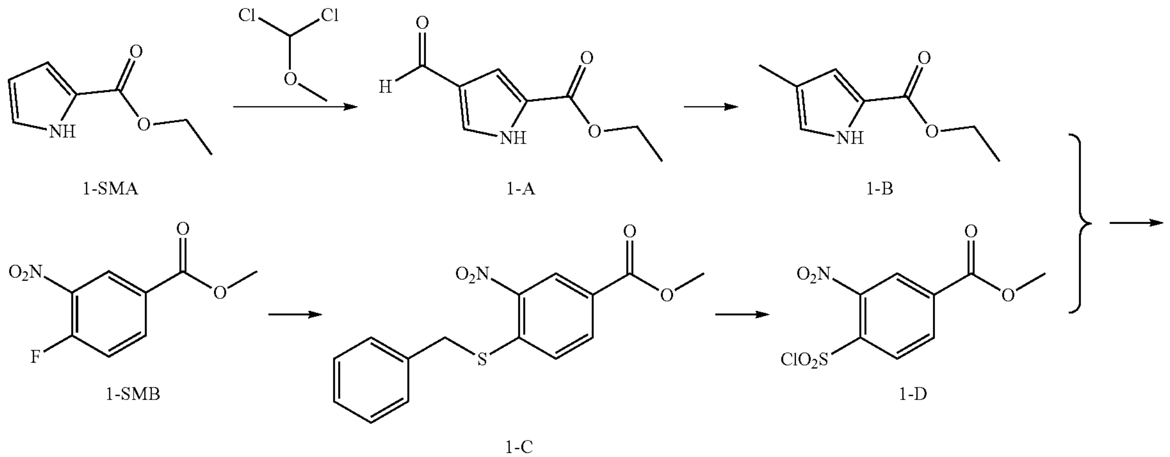
1-SMA 1-A 1-B
1-SMB 1-C 1-D
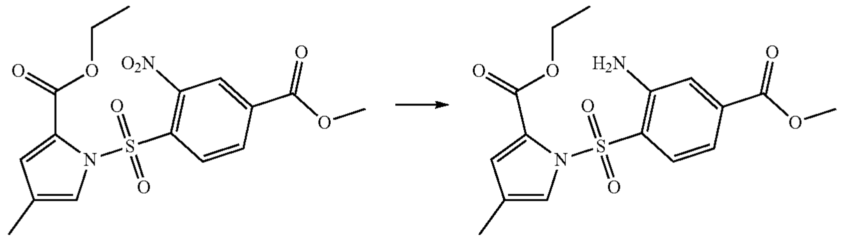
1-E 1-SM1
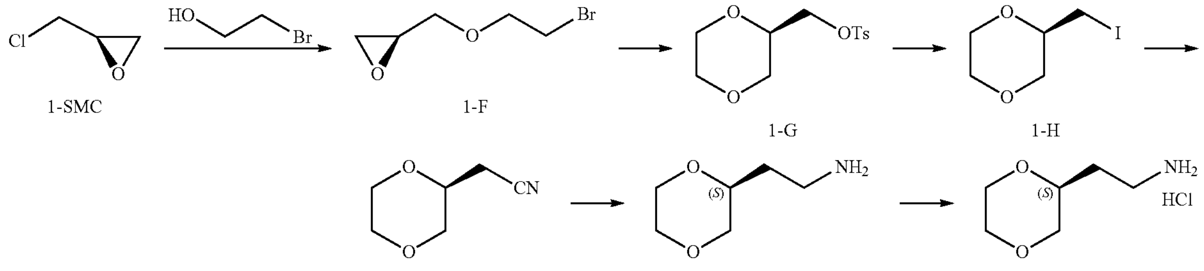
1-SMC 1-F 1-G 1-H
1-I 1-J 1-SM2
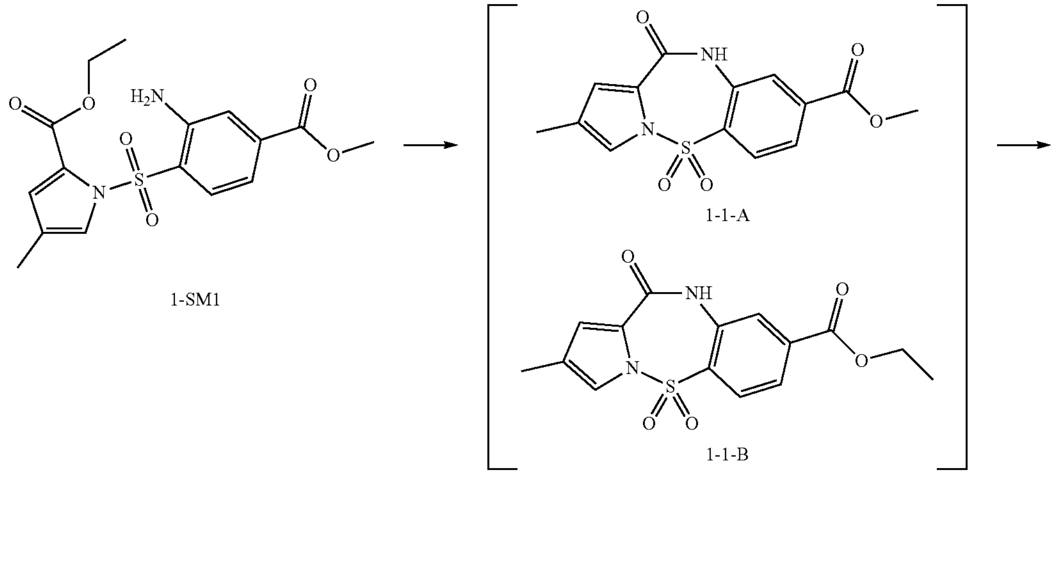
1-SM1 1-1-A 1-1-B -continued

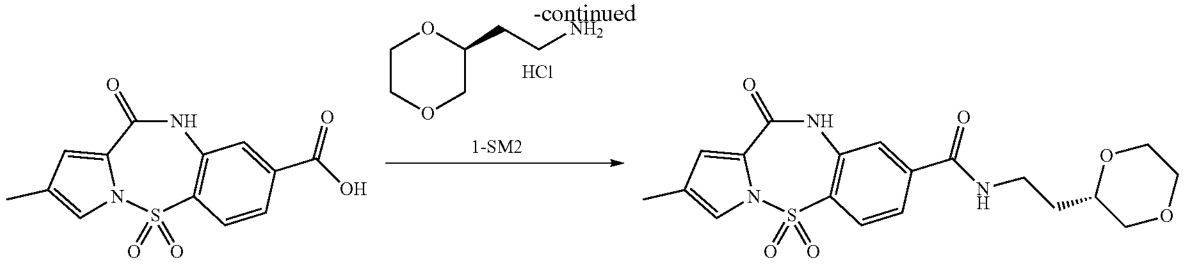

1-2 1

Step 1: Synthesis of Compound 1-A

Anhydrous dichloromethane (5 L) was added into a dry three-necked flask (10 L) and stirred, then compound 1-SMA (500.00 g) and nitromethane were added into the three-necked flask successively to obtain a mixture. The mixture was placed in a dry ice ethanol bath, and cooled to −10° C. The temperature was controlled between −10° C.-0° C. Aluminum trichloride (1.15 kg) was slowly added into the reaction flask and the temperature was controlled to less than −0° C. Next, α,α-dichlorodimethyl methyl ether (495.00 g) was slowly added into the reaction kettle to obtain a reaction solution, which was slowly heated to room temperature and stirred for 18 hours. TLC (PE:EA 3:1) monitoring revealed the disappearance of the raw material spot and the appearance of a new spot with high polarity. Potassium bisulfate solution (3 L) was slowly added dropwise to the extracted reaction solution to a concentration of 10%, stirred for 20 minutes while crushed ice was added to prevent overheating. The mixed solution was transferred to a 25 L separatory funnel and allowed to stand for stratification to separate the dichloromethane layer, and the aqueous phase was extracted with dichloromethane (2 L*2). After washing with 10% potassium bisulfate solution (5 L*2), the organic phase was separated and dried with anhydrous sodium sulfate (1 kg). The organic phase was concentrated under reduced pressure to obtain compound 1-A as a dark-green solid.

$^1$H NMR (400 MHz, deuterated chloroform) 6=9.97 (br s, 1H), 9.87-9.82 (m, 1H), 7.58 (dd, J=1.5, 3.3 Hz, 1H), 7.36-7.29 (m, 1H), 4.37 (q, J=7.1 Hz, 2H), 1.38 (t, J=7.2 Hz, 3H).

Step 2: Synthesis of Compound 1-B p-toluenesulfonyl hydrazide (2.23 kg, 11.96 mol) was added into the THF (20 L) solution containing compound 1-A (2 kg, 11.96 mol). The solution was stirred at 20° C. for about 1 h. When the disappearance of the raw material was monitored by TLC, the reaction system was heated to 60° C., and sodium cyanoborohydride (902 g, 14.36 mol) was added in batches. After the addition, the reaction solution was heated to 70° C. and stirred for 3 h. After the heating was stopped and cooled down to room temperature, 5 L of water was added to quench the reaction, followed by removing most of the THF under reduced pressure, and the residue was extracted with a large amount of EA (1.5 L*3). The organic phases were pooled, washed with saturated sodium chloride and dried with anhydrous sodium sulfate. Then the organic phases were filtered, and the solvent was removed under reduced pressure. Finally, the crude product was column chromatographed to obtain compound 1-B as a pale-yellow solid.

Step 3: Synthesis of Compound 1-C

Methanol (32 L) was added into a 50 L jacketed kettle and stirred, then compound 1-SMB (4000.00 g) and diisopropylethylamine (5.25 L) were added successively, and the internal temperature was reduced to 5-10° C. Benzyl mercaptan (2490.00 g) was slowly added dropwise, and the internal temperature was maintained at 5-15° C. After the addition was complete, the cooling system was turned off to let the temperature rise naturally, and stirring was continued for 2.5 h. Next, stirring was stopped, the speed was adjusted to 100 rpm, and the reaction liquid was released and filtered through a desktop filter to obtain a filter cake. The filter cake was washed three times with water (5 L), followed by once with EtOH (3 L). The filter cake was filtered by suction filtration until it was no longer viscous, thereby obtaining compound 1-C as a pale-yellow solid.

Step 4: Synthesis of Compound 1-D

Dichloromethane (7.5 L) was added into a 50 L kettle and stirred, then compound 1-C (1500 g) was added. The internal temperature was reduced to 0-10° C., and HCl solution (6 M, 4.12 L) was added. The sodium hypochlorite solution (commercially available 8% solution, 23.0 kg) was added dropwise under 0-10° C. with the lid open. After dropwise addition, the cooling system was turned off and stirring was continued for about 17 hours with the lid open. Then sodium bisulfite was added for heat capacity (1000 g, 5 L aqueous solution), and starch potassium iodide test paper was used to detect if there is no oxidant remaining in the water phase. Next, stirring was stopped, the solution was allowed to stand for stratification. The dichloromethane layer was collected while the aqueous layer was extracted with dichloromethane (2.5 L), and the dichloromethane layers were pooled. The organic phase was dried with anhydrous sodium sulfate and filtered, then the solvent was removed under reduced pressure to obtain compound 1-D as a white solid.

$^1$H NMR (400 MHz, deuterated chloroform) δ=8.50-8.43 (m, 2H), 8.34 (d, J=8.2 Hz, 1H), 4.04 (s, 3H).

Step 5: Synthesis of Compound 1-E

Tetrahydrofuran (10 L) was added into a dry 50 L jacketed kettle and stirred, then compound 1-B (2000 g) was added. The internal temperature was reduced to 0-10° C. The temperature was maintained at 0-15° C. in about 1.5 hours, and potassium tert-butoxide (1 M THF solution, 15.67 L) was added. After addition, the temperature was raised to about 20° C. and the stirring was continued for 1 hour. Next, the temperature was reduced to 0-10° C., and the THF (10 L) solution containing compound 1-D (4380 g) was slowly added. After addition, the temperature was slowly raised to 15° C. and the stirring was continued for about 16 hours. Ethyl acetate (10 L) was added for extraction, and the organic phase was washed with saturated sodium chloride solution (10 L) twice. The aqueous phases were combined and extracted with EA (5 L), and the organic phases were combined. Finally, the solvent was removed from the organic phase under reduced pressure to obtain compound 1-E as a pale-yellow solid.

$^1$H NMR (400 MHz, DMSO-$d_6$) δ=8.55 (d, J=1.4 Hz, 1H), 8.37 (dd, J=1.5, 8.3 Hz, 1H), 7.91 (d, J=8.3 Hz, 1H), 7.60 (s, 1H), 7.13 (d, J=1.8 Hz, 1H), 4.02 (q, J=7.0 Hz, 2H), 3.93 (s, 3H), 2.10 (s, 3H), 1.08 (t, J=7.1 Hz, 3H).

Step 6: Synthesis of Compound 1-SM1

Compound 1-E (1000.0 g) was added into a dry 10 L three-necked flask and stirred, then glacial acetic acid (5 L) was added and the internal temperature of the reaction was controlled at 25-30° C. Iron powder (1 eq, 140.9 g) was slowly added. After stirring for 30 minutes, the second batch of iron powder (0.5 eq, 70.44 g) was slowly added. After continuing stirring for 30 minutes, the third batch of iron powder (0.5 eq, 70.44 g) was added. After another 30 min of stirring, the fourth batch of iron powder (0.5 eq, 70.44 g) was added, and the reaction continued to be stirred until the disappearance of raw material and the appearance of anew point with high polarity were monitored. Next, stirring was stopped, and the reaction solution was transferred to 25 L dispenser for liquid separation. 10 L of ethyl acetate was added to the solution, which was then washed with 5 L saturated sodium bisulfate aqueous solution twice. After the liquid separation, the aqueous phase was back-extracted with 5 L of ethyl acetate. The organic phases were then combined and washed with 10% NaOH aqueous solution until pH>8, and the organic phase was collected by liquid separation. The organic phase was concentrated under reduced pressure to obtain compound 1-SM1 as a white solid.

$^1$H NMR (400 MHz, DMSO-$d_6$) δ=7.79-7.71 (m, 2H), 7.50 (d, J=1.8 Hz, 1H), 7.14 (dd, J=1.7, 8.5 Hz, 1H), 6.96 (d, J=2.0 Hz, 1H), 6.42 (s, 2H), 4.11 (q, J=7.2 Hz, 2H), 3.84 (s, 3H), 2.04 (s, 3H), 1.16 (t, J=7.1 Hz, 3H).

Step 7: Synthesis of Compound 1-F

Toluene (12 L) was added to a dry 50 L jacketed kettle and stirred, then 2-bromoethanol (9930 g) was added, followed by boron trifluoride ether (268 g). The reaction was heated to 30-35° C. Compound 1-SMC (3500 g) was slowly added dropwise, and the addition was completed in about 1.5 hours. After addition, the internal temperature of the reaction was raised to about 55-65° C. and the temperature setting of heater was adjusted to 60° C. to keep the internal temperature at 55-65° C. for 1 hour. Then the internal temperature of the system was reduced to about 10° C., and sodium hydroxide aqueous solution (3783 g, water 17.5 L) at about 20° C. was slowly added into the reaction system while the internal temperature was maintained at 10-20° C. After the addition of NaOH solution, the temperature control of the heater was turned off, and the reaction continued to stir for about 16 h. Then the stirring was stop that the reaction solution was allowed to stand for stratification. The aqueous layer was extracted with 2-methyltetrahydrofuran (10 L) and the organic phases were combined, washed with water (10 L) and allowed to stand for stratification to collect organic phase. The organic phase was finally concentrated under reduced pressure to obtain compound 1-F as a colorless oil. $^1$H NMR (400 MHz, deuterated chloroform) δ=3.87-3.71 (m, 4H), 3.66-3.59 (m, 3H), 3.42 (dd, J=6.0, 11.7 Hz, 1H), 3.20-3.13 (m, 1H), 2.79 (t, J=4.6 Hz, 1H), 2.65-2.59 (m, 1H).

Step 8: Synthesis of compound 1-G

An aqueous solution of sodium hydroxide (3240 g, 15 L of water) was added into a 50 L jacketed kettle, compound 1-F (4430 g) was then added and the heating was turned on. After the reaction was heated to 90° C., the stirring was continued for 1 h. The cooling was turned on to reduce the reaction to about 15° C., then THF solution (6180 g, THF: 15 L) containing p-toluenesulfonyl chloride was added. The temperature control of the heater was turned off, and the reaction was further stirred at about 15° C. for about 16 h. Next, the stirring was stopped to let the reaction allowed to stand for stratification. The aqueous phase was extracted with 2-methyltetrahydrofuran (10 L), and the 2-methyltetrahydrofuran phase (there was white insoluble matter, which disappeared after the washing) was washed with water (5 L), and the organic phases were combined. DMAP (500 g) and triethylamine (2.5 L) were added to the organic phase, followed by stirring the organic phase for 30 minutes. Then the organic phase was washed with saturated sodium chloride solution (10 L) and allowed to stand for stratification, and the aqueous phase was discarded. The organic phase was washed with potassium hydrogen sulfate solution (3800 g, 15 L of water) and saturated sodium chloride solution (5 L*twice) successively, and then allowed to stand for stratification, and the organic phase was collected. The organic phase was finally concentrated under reduced pressure to remove the solvent to obtain the crude product compound 1-G. $^1$H NMR (400 MHz, deuterated chloroform) δ=7.77 (d, J=8.3 Hz, 2H), 7.34 (d, J=8.2 Hz, 2H), 4.03-3.91 (m, 2H), 3.80-3.49 (m, 8H), 3.33 (dd, J=9.9, 11.4 Hz, 1H), 2.43 (s, 3H).

Step 9: Synthesis of Compound 1-H

Acetone (30 L) was added into a clean 50 L jacketed kettle and stirred, then compound 1-G (4500 g) was added, followed by sodium iodide (6190 g). The heating was turned on, and after the reaction was heated to 75° C., the stirring was continued for 16 hours. After being cooled to room temperature, the reaction was filtered, and the filtrate was concentrated under reduced pressure at 50° C. Ethyl acetate (15 L) and water (10 L) were added to the concentrated crude product, and the mixture was stirred and then allowed to stand for stratification. The organic phase was washed with 0.5 M sodium thiosulfate (10 L). The aqueous phase and sodium thiosulfate solution were combined and extracted with EtOAc (5 L). The organic phases were combined and washed with saturated sodium chloride solution (10 L), then allowed to stand for stratification, and the organic phase was collected. The organic phase was finally concentrated under reduced pressure to remove the solvent to obtain the crude product compound 1-H. $^1$H NMR (400 MHz, deuterated chloroform) δ=3.90-3.83 (m, 2H), 3.81-3.75 (m, 2H), 3.74-3.65 (m, 5H), 3.63-3.49 (m, 7H), 3.31-3.18 (m, 3H), 3.06-3.04 (m, 2H).

Step 10: Synthesis of Compound 1-I

DMSO (20 L) was added into a clean 50 L jacketed kettle and stirred, then compound 1-H (4700 g) was added and the temperature was raised to 35° C., followed by adding sodium cyanide (1010 g). The internal temperature of the reaction was raised to about 60° C. within 20 minutes, then the temperature was gradually reduced to 35° C., and the stirring was continued for about 16 hours. Sodium bicarbonate solution (2000 g sodium bicarbonate, 10 L of water) was added to the reaction system, which was then stirred for about 5 minutes. EtOAc: MeOH (20 L, 2 L) was added and the reaction system was further stirred for 2 minutes, followed by standing for about 1 hour. Next, the reaction system was partitioned and about 30 L of the lower layer solution was separated. The lower layer solution was extracted twice with EtOAc:MeOH (15 L:1.5 L for the first time, and 5 L:0.5 L for the second time). After the extraction, the upper organic phase and the upper layer of the remaining reaction liquid were combined, washed three times with saturated sodium chloride solution (10 L each), and allowed to stand for stratification. The aqueous phase was discarded while the organic phase was collected. Finally, the solvent was removed from the organic phase under reduced pressure, and the crude product was column chromatographed to obtain compound 1-I as a colorless oil. $^1$H NMR (400 MHz, deuterated chloroform) δ=3.84-3.65 (m, 6H), 3.61-3.53 (m, 2H), 3.35 (t, J=10.5 Hz, 1H), 2.49-2.44 (m, 2H).

Step 11: Synthesis of Compound 1-J

Under the protection of argon, Raney nickel (10.00 g, 116.73 mmol) and EtOH (150 mL) were added into the dry hydrogenation flask, and then 1-I (20 g, 157.31 mmol) and $NH_3 \cdot H_2O$ (13.65 g, 97.36 mmol, 15.00 mL, 25% purity) were added, followed by replacement, and the reaction was stirred at 50 psi and 50° C. for 3.5 h. The reaction solution was filtered using diatomite, and the filtrate was concentrated under reduced pressure to obtain compound 1-J as a yellow oil. $^1$H NMR (400 MHz, deuterated chloroform) δ=3.82-3.57 (m, 6H), 3.34-3.18 (m, 1H), 2.86-2.72 (m, 2H), 1.60-1.38 (m, 2H).

Step 12: Synthesis of Compound 1-SM2

1-J (800.00 g) was added into a 5 L three-necked flask and stirred, then ethyl acetate (800 mL) was added within 0.5 h, and 4M HCl/EtOAc (1.6 L) was slowly added dropwise till the pH of the system was smaller than 5 while the internal temperature was maintained at 5-15° C. Next, the cooling system was turned off, and the reaction was heated to room temperature and further stirred for 1 hour. After stopping the stirring, the reaction was filtered through a desktop filter to obtain a filter cake, which was then concentrated under reduced pressure (40-45° C.) to obtain a crude product. Acetonitrile (2 mL/g) was added to the preceding product and the mixture was slurried for 1 hour. After the slurried product was filtered, the filter cake was collected separately, and the organic solution was removed under reduced pressure to obtain a white solid compound 1-SM2. $^1$H NMR (399 MHz, METHANOL-$d_4$) δ=3.88-3.72 (m, 5H), 3.67-3.59 (m, 1H), 3.36-3.31 (m, 1H), 3.14 (t, J=6.7 Hz, 2H), 1.87-1.67 (m, 2H).

Step 13: Synthesis of Compound 1-1-A and Compound 1-1-B

Toluene (20 L) was added into a dry 50 L jacketed kettle and stirred, then compound 1-SM1 (2500 g), and the internal temperature was raised to 30-35° C. The inert gas environment in the kettle was maintained by nitrogen purging. Then trimethylaluminum (3.0 L, the temperature in the kettle rises slowly with the addition of $Al(CH_3)_3$) was added dropwise. After addition, the nitrogen purging was turned off. The temperature was raised to 80-85° C. and the reaction was further stirred about 16 hours. Next, the cooling was turned on to reduce the temperature of the reaction to 20-30° C. Half of the reaction solution (about 12 L), to which EtOAc (10 L) was added, was transferred and mixed well. The mixed solution was added to 10% $KHSO_4$ solution (10 L) while stirring, stirred for 2 minutes and then allowed to stand for stratification. The organic layer was washed with 10% $KHSO_4$ solution (10 L), the water phases were combined and extracted twice with DCM (each 7.5 L). The other half of the reaction solution (about 12 L) was transferred out, which was treated in the same way as defined above. Then the organic phases were combined and concentrated under reduced pressure to obtain a crude product. Two times the volume of n-heptane was added and beaten for 1 hour to form a slurry. The slurry was filtered, and vacuum-dried for >12 hours at 40° C., P≤−0.1 MPa. A mixture of compound 1-1-A and compound 1-1-B was obtained.

Step 14: Synthesis of Compound 1-2

Tetrahydrofuran (3840 mL) was added into a 10 L three-necked flask and stirred, and the mixture of compound 1-1-A and compound 1-1-B (480.00 g) was added slowly, then $H_2O$ (960 mL) solution of $LiOH \cdot H_2O$ (118.84 g) was added dropwise slowly. After addition, the temperature was raised to 60° C. and the reaction was stirred for 1 hour. Then concentrated HCl was added to the reaction solution to adjust the pH of the system to 2, and stop stirring. Next, the solution was left standing for liquid stratification. The aqueous phase was extracted twice with THF (600 mL), and the organic phases were combined and concentrated under reduced pressure (40-45° C.). The solid was slurried with pure water (2 mL/g) for 0.5 hours and filtered, and the filter cake was vacuum-dried for over 12 hours at 40° C. and P≤−0.1 MPa to obtain compound 1-2. $^1$H NMR (399 MHz, DMSO-$d_6$) δ=11.19 (s, 1H), 8.09 (d, J=8.2 Hz, 1H), 8.00 (d, J=1.6 Hz, 1H), 7.88 (dd, J=1.5, 8.3 Hz, 1H), 7.39 (dd, J=1.2, 2.0 Hz, 1H), 7.01 (d, J=2.0 Hz, 1H), 2.05 (s, 3H).

Step 15: Synthesis of Compound 1

DMF (2.25 L) was added into a 5 L three-necked flask and stirred, then compound 1-2 (400.00 g) and HATU (744.83 g) were added successively and stirred for 30 min, followed by compound 1-SM2 (229.86 g). DIPEA (568.68 mL) was slowly added dropwise at room temperature within 1 hour. After addition, the reaction was further stirred at room temperature for 16 hours. Next, the reaction solution was transferred to a separatory funnel, ethyl acetate (2 L) and pure water (1 L) were added, and the solution was stirred for 2 min and then left standing for stratification to separate the water phase. Then pure water (1 L) was added to wash the organic phase which was then stirred and allowed to stand for stratification. The combined aqueous phase was extracted three times with EtOAc (500 mL), and the organic phases were combined. The organic phase was washed twice with sodium carbonate solution (1.5 L), twice with potassium hydrogen sulfate solution (1 L) and twice with pure water (1 L), successively. The organic phase was concentrated under reduced pressure (40-45° C.) to obtain a crude product. Ethyl acetate (2 mL/g) was added to the crude product and the mixture was slurried for 1 hour. Finally, the slurried mixture was filtered and the filter cake was collected to obtain compound 1. $^1$H NMR (400 MHz, DMSO-$d_6$) (=11.13 (br s, 1H), 8.73 (br t, J=5.5 Hz, 1H), 8.05 (d, J=8.2 Hz, 1H), 7.83 (d, J=1.3 Hz, 1H), 7.74 (dd, J=1.5, 8.4 Hz, 1H), 7.36 (s, 1H), 6.98 (d, J=2.0 Hz, 1H), 3.71-3.48 (m, 5H), 3.45-3.31 (m, 1H), 3.45-3.30 (m, 1H), 3.27-3.21 (m, 1H), 3.14 (dd, J=9.9, 11.2 Hz, 1H), 2.03 (s, 3H), 1.53 (q, J=7.0 Hz, 2H).

Biological Test Experiment

Experimental Example 1: Compound 1 and Tenofovir Disoproxil Fumarate (Tenofovir Difumarate Fumarate, TDF) Combined Drug In Vitro on HBV Inhibitory Activity 1. Experimental Method 1.1 Day 1, HepG2.2.15 cells were seeded into a 96-well cell culture plate at a density of 40,000 cells/well, and then the cells were cultured overnight at 5% $CO_2$ and 37° C.

1.2 Day 2, the compound 1 and TDF were combined with 7 different concentrations (selected about 8×, 4×, 2×, 1×, 0.5×, 0.25×, 0.125×$EC_{50}$ concentration gradient) for orthogonal proportioning, and added to 96-well plate, each combination is 3 double plates, and the final concentration of DMSO is 0.5%. The detection concentration of each compound is shown in Table 1.

1.3 Day 5, the cell supernatant was discarded, a fresh medium containing the compound was added, and the cells were cultured under 5% $CO_2$, 37° C. for 3 days. On the 8th day, the supernatant from the cell plate treated with the compound was extracted according to the QIAamp 96 DNA Blood Kit (12) instruction.

1.4 HBV DNA was quantified by qPCR method. HBV plasmid DNA is used as the standard. The concentration of standard HBV plasmid DNA starts from 107 copies/μL with 10-fold dilution at 7 points. Fit the standard curve with the HBV DNA copy number and CT value of each standard, and calculate the HBV DNA copy number in each test sample.

MacSynegy software (Prichard et al., 1990) was used to process the HBV DNA copy number test data and analyze the effect parameters of compound 1 and TDF in combination. The CellTiter-Glo kit was used to detect the cytotoxicity of the compounds to HepG2.2.15 cells. According to the kit instructions, use a multifunctional microplate reader to detect the chemiluminescence intensity (RLU) of each cell well.

TABLE 1

The detected concentrations of compounds in the combination test

| Compound | Detection of final concentration (nM) | | | | | | |
|---|---|---|---|---|---|---|---|
| Compound 1 | 34.09 | 17.04 | 8.522 | 4.261 | 2.131 | 1.065 | 0.533 |
| TDF | 64 | 32 | 16 | 8 | 4 | 2 | 1 |

2. Result

HepG2.2.15 cells were used to evaluate the inhibitory activity of compound 1 and TDF in vitro on HBV. The inhibitory activity and cytotoxicity results of the combined drugs on HBV are summarized in Table 2, and the combined drug effect diagram is shown in FIG. 1.

The experimental results showed that the synergy index and antagonism index of the combination of compound 1 and TDF in vitro in 95% confidence space were 13.27 and −1.74, respectively, showing an additive effect. None of the compounds showed cytotoxicity in the tested concentrations (see Table 3).

TABLE 2

Inhibitory activity of compound 1 and TDF in vitro on HBV

| Compound a | Compound b | Synergy index (95% confidence interval) | Antagonism index (95% confidence interval) | Combined drug effect |
|---|---|---|---|---|
| Compound 1 | TDF | 13.27 | −1.74 | Additive effect |

Note:
Description of drug combination index: if the index is positive, it is synergistic, and if it is negative, it is antagonistic; the absolute value of the index is less than 25, that is, the additive effect; the absolute value of the index is in the range of 25-50, that is, mild but clear synergy or Antagonistic effect; the absolute value of the index is in the range of 50-100, that is, moderate synergistic or antagonistic effect, which may have important significance for in vivo effects. The absolute value of the index is in the range of >100, that is, a highly synergistic or antagonistic effect, which is likely to have important meanings in vivo.

TABLE 3

[]The average cell viability percentage (%) of the cytotoxicity test of the combination drug

| Compound | Concentration (nM) | Compound 1 | | | | | | | |
|---|---|---|---|---|---|---|---|---|---|
| | | 34.09 | 17.04 | 8.522 | 4.261 | 2.131 | 1.065 | 0.533 | 0 |
| TDF | 64 | 125.9 ± 24.5 | 129.7 ± 27.6 | 130.7 ± 24.6 | 132.7 ± 24.6 | 131 ± 26.9 | 133.6 ± 26.2 | 130.4 ± 17.9 | 127 ± 14 |
| | 32 | 113.2 ± 18.7 | 112.4 ± 18.4 | 108.4 ± 15.8 | 112.1 ± 18.8 | 111.7 ± 18.3 | 112.8 ± 16.2 | 111.7 ± 13.1 | 111 ± 7.3 |
| | 16 | 109.2 ± 18.3 | 112.5 ± 19.4 | 113 ± 19 | 117.2 ± 21.7 | 114.9 ± 16.6 | 113.8 ± 15.3 | 115.5 ± 10.6 | 111.4 ± 7.7 |
| | 8 | 113.3 ± 20.2 | 114.8 ± 18.5 | 119 ± 21.7 | 119.4 ± 19.4 | 124.3 ± 15.7 | 122.6 ± 13.6 | 123.5 ± 10.4 | 116.6 ± 10.9 |
| | 4 | 102.5 ± 15.8 | 102.5 ± 15.4 | 104.6 ± 15.5 | 106.9 ± 12.6 | 110.2 ± 9.6 | 111.2 ± 8 | 108.1 ± 4.7 | 103.8 ± 6 |
| | 2 | 102. 1 ± 13.6 | 101.9 ± 16.3 | 105 ± 15.9 | 107.3 ± 15 | 105.7 ± 10.4 | 102.2 ± 8.7 | 103.2 ± 2.8 | 101.1 ± 2.9 |

TABLE 3-continued

[]The average cell viability percentage (%) of the cytotoxicity test of the combination drug

| | | Compound 1 | | | | | | | |
|---|---|---|---|---|---|---|---|---|---|
| Compound | Concentration (nM) | 34.09 | 17.04 | 8.522 | 4.261 | 2.131 | 1.065 | 0.533 | 0 |
| | 1 | 105.5 ± 16.7 | 106.9 ± 17 | 106.1 ± 19.4 | 107.2 ± 14.9 | 109.8 ± 12.3 | 108.3 ± 7.3 | 105.2 ± 6.3 | 103.1 ± 7.8 |
| | 0 | 115.2 ± 17.1 | 123.1 ± 20.4 | 124.3 ± 14.8 | 125.1 ± 11.9 | 124.5 ± 8.9 | 128.1 ± 3.7 | 121.5 ± 7.1 | 120.9 ± 5.2 |

3. Conclusion

The combination of compound 1 and TDF in vitro showed an additive effect on the inhibitory activity of HBV, and the compound showed no cytotoxicity in the tested concentration. The test results support the combined application of compound 1 and TDF in the clinical treatment of patients with chronic HBV infection.

Experimental Example 2: Using AAV/HBV Mouse Model to Evaluate the Anti-Hepatitis B Virus Efficacy of the Test Compound In Vivo Experimental Materials Animals 5-week-old male C57BL/6 mice without specific pathogen level, purchased from Shanghai Slack Laboratory Animal Co., Ltd.

2. Solvents and Compounds

Solvent: 10% solutol aqueous solution

Test Compound:

Compound 1 was added with an appropriate amount of the above-mentioned solvent, and a uniform particle suspension was obtained after vortexing, and the preparation concentration was 1.0, 3.0 and 10.0 mg/mL. Store at 4° C. until used. Compound 1 is calculated according to the salt coefficient of 1.0 and the purity of 100%.

Tenofovir disoproxil (TDF) was purchased from Shanghai Panhong Chemical Technology Co., Ltd. Weigh an appropriate amount of TDF and dissolve it in physiological saline to prepare a 1 mg/mL mother liquor, vortex until TDF is fully dissolved, dispense into 1 mL size and store at −20° C. Take 1 mL of mother liquor before each administration, and dilute the working solution 10 times to 0.1 mg/mL with normal saline for the day's administration.

Recombinant Virus rAAV8-1.3HBV rAAV8-1.3HBV (Type D, ayw) was purchased from Beijing Wujiahe Institute of Molecular Medicine, batch number x2018032301, $1\times10^{12}$ viral genome (v.g.)/mL. Dilute with sterile PBS to $5\times10^{11}$ v.g./mL before the experiment. Each mouse was injected with 200 μL, that is, each mouse was injected with $1\times10^{11}$ v.g.

3. Test Method

Establishment of AAV/HBV Mouse Model

AAV/HBV injection: rAAV8-1.3HBV is pre-prepared with sterile PBS to a concentration of $1\times10^{11}$ v.g./200 μL solution before injection.

Infection level detection: On days 14 and 21 after virus injection, about 120 μL of blood was collected from the submandibular vein for all infected mice to collect serum. After the whole blood was incubated in a 37° C. incubator for 30 minutes, the blood was centrifuged at 13,200×g for 3 minutes at 4° C. to collect about 30 μL of serum. The serum is stored at −80° C. for the detection of HBV DNA, HBeAg and HBsAg.

Grouping: On the 28th day after virus injection, according to the levels of HBV DNA, HBsAg and HBeAg in serum samples on the 14th and 21st days after virus injection, and the body weight of the mice.

Definition of experimental days: the day of the first dosing is set to day 0 of the experiment.

4. In Vivo Experiment Design

In vivo experimental dosing and sampling plan are shown in Table 4

TABLE 4

[] In vivo experimental dosing and sampling plan

| | | Dosing | | | | Sample collection | | |
|---|---|---|---|---|---|---|---|---|
| | | | | | | Non-end point | | |
| Group | Number of animals | Compound name | Dosage (mg/kg) | Dosing (mL/kg) volume | Frequency Dosage of oral | Virology testing | Drug metabolism testing | End point |
| 1 | 8 | Solvent | 0 | 10 | 2 times a day (BID), days 0-27 | Serum was collected on day 0 (before dosage), 3, 7, and 14 days. | Group 2: On the 27th day 0 hours (before dosage), 1.4, 8, 9, 12 and 24 hours after the first dosage, blood was | On the 28th day, serum and liver samples were collected. |
| 2 | 8 | Compound 1 | 10 | 10 | 2 times a day, days 0-27 | | | |
| 3 | 8 | Compound 1 | 30 | 10 | 2 times a day, days 0-27 | | | |
| 4 | 8 | Compound 1 | 100 | 10 | 2 times a day, days 0-27 | | | |

TABLE 4-continued

[] In vivo experimental dosing and sampling plan

| Group | Number of animals | Compound name | Dosage (mg/kg) | Dosing (mL/kg) volume | Frequency Dosage of oral | Virology testing | Drug metabolism testing | End point |
|---|---|---|---|---|---|---|---|---|
| | | Dosing | | | | Sample collection: Non-end point | | Sample collection |
| 5 | 8 | TDF | 1 | 10 | 1 time a day, days 0-27 | | collected to collect plasma. | |
| 6 | 8 | Compound 1 | 10 | 10 | 2 times a day, days 0-27 | | | |
| | | TDF | 1 | 10 | 1 time a day, days 0-27 | | | |

Serum sample preparation: After the blood sample was incubated at 37° C. for about 30 minutes, centrifuged at 4° C., 13,200 g for 3 minutes, and the separated supernatant was quickly frozen in dry ice.

Plasma sample preparation and pretreatment: After the blood sample was anticoagulated with K2EDTA, the supernatant was separated by centrifugation at 4° C. and 7,000 g for 10 minutes. The separated plasma was added with precipitant, [methanol: acetonitrile (v: v, 50:50) solution] at a ratio of 1:20, vortexed to mix, and quickly frozen in dry ice.

Body weight recording. During the in vivo experiment, the status of the mice was regularly observed, and the weight of the mice was recorded on the day of infection, dosage, blood sampling and the end of the experiment.

Blood was collected from the heart to collect serum for HBV DNA detection and detection of HBV RNA levels in groups 1 and 4.

5. Sample Analysis

1. HBsAg ELISA (Antu Biological, CL 0310) kit instructions for detecting HBsAg content in mouse serum;

2. Instructions for HBeAg ELISA kit (Antu Biotech, CL 0312), to detect HBeAg content in mouse serum;

3. Quantitative PCR detection of HBV DNA content in mouse serum and liver:

TABLE 5 qPCR reaction component list

| PCR reaction solution composition | Required volume of 1 reaction system (μL) |
|---|---|
| Taqman Universal Master Mix (2X) | 5 |
| Forward primer (10 μM) | 0.4 |
| Reverse primer (10 μM) | 0.4 |
| Probe (10 μM) | 0.2 |
| AE buffer | 2 |
| Sample | 2 |

Data analysis: The data is expressed as the average value standard error of each group of samples. Unless otherwise specified, groups 1-6: n=8. Use Student's t test for statistical analysis.

6. Results

1) The Effect of Test Compound on Serum HBV DNA in AAV/HBV Mouse Experiment

Figure 2:
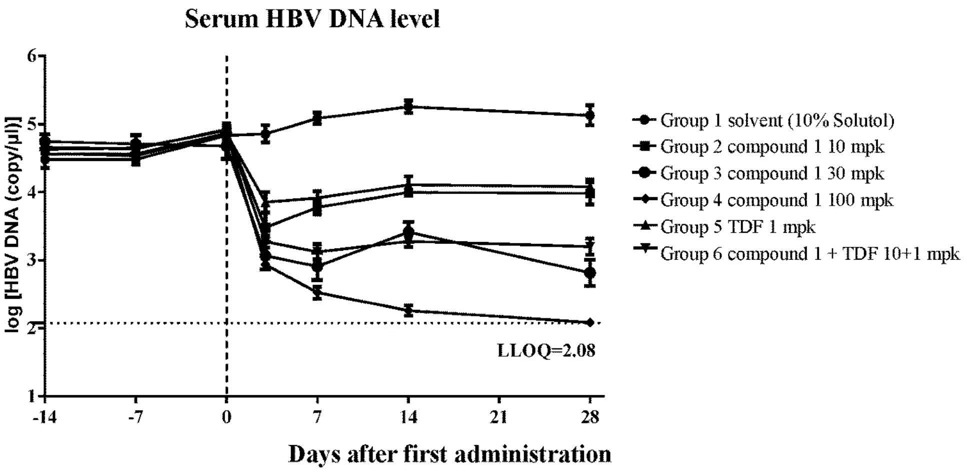
FIG. 2: the effect of the treatment of test compound for 28 days on AAV/HBV mouse serum HBV DNA.

The content of serum HBV DNA in each group of mice is summarized in FIG. 2:

The serum HBV DNA content of mice in the solvent group (Group 1) remained stable after dosage. Compound 1 single-drug group: Compared with the solvent group (Group 1), compound 1 was low (10 mpk, Group 2) and medium (30 mpk). The HBV DNA content in the serum of mice in the high (100 mpk) three dose groups began to show a dose-dependent trend after 3 days of dosage, and the HBV DNA content of the low and medium dose groups remained stable after 7 days of dosage; the serum HBV DNA content in the dose group continued to decrease for 7-28 days after dosage, which was significantly lower than that in the solvent group ($p<0.01$).

Compound 1 and TDF combined dosage group (Group 6, 10+1 mpk): Compared with the solvent group (Group 1), the HBV DNA content in the serum of mice decreased after 3 days of dosage, and the level of serum was 7-28 days after dosage. The HBV DNA content remained stable. Compared with compound 1 (Group 2, 10 mpk) and TDF (Group 5, 1 mpk) single-agent groups, the combined dosage showed a significant reduction in serum HBV DNA content in mice ($p<0.01$).

2) The Effect of Test Compound AAV/HBV on HBV DNA in Liver in Mice

Figure 3:
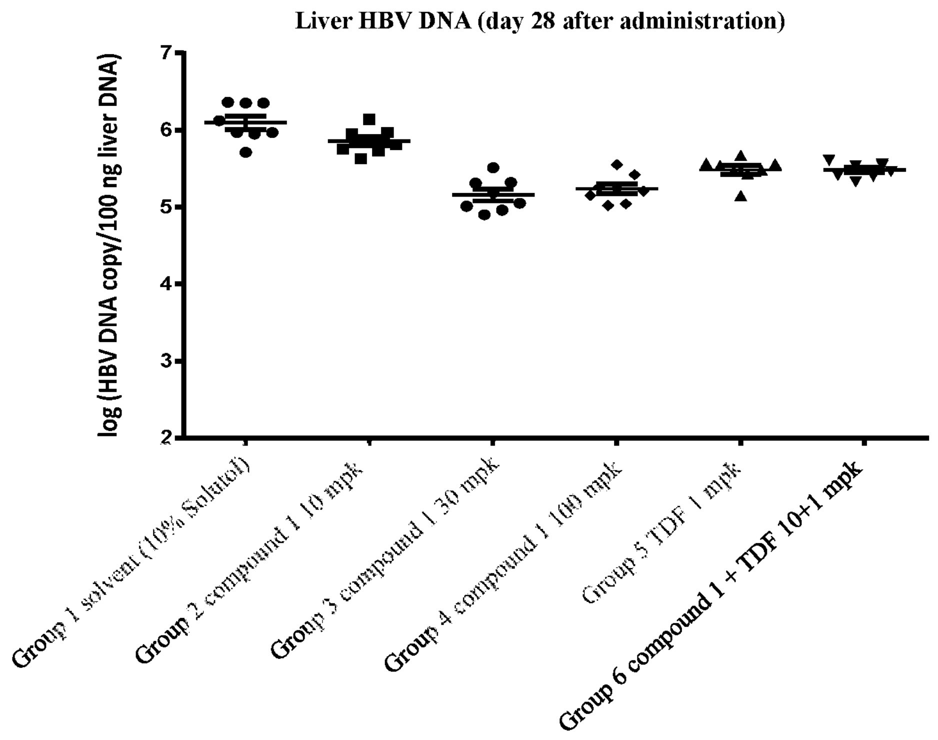
FIG. 3: the effect of the treatment of test compound on AAV/HBV mouse liver HBV DNA.

The content of HBV DNA in the liver of mice in each group is summarized in FIG. 3:

Compared with the solvent group (Group 1), after 28 days of dosage, the HBV DNA content in the liver of mice in the low (10 mpk), medium (30 mpk), and high (100 mpk) dose groups of Compound 1 all decreased. In the compound 1 and TDF combined dosage group (Group 6, 10+1 mpk) 28 days after dosage, the HBV DNA content in the liver was significantly lower than that in the compound 1 10 mpk single drug group ($p<0.001$).

3) The Effect of Test Compound on Serum HBV RNA in AAV/HBV Mouse Experiment

Figure 4:
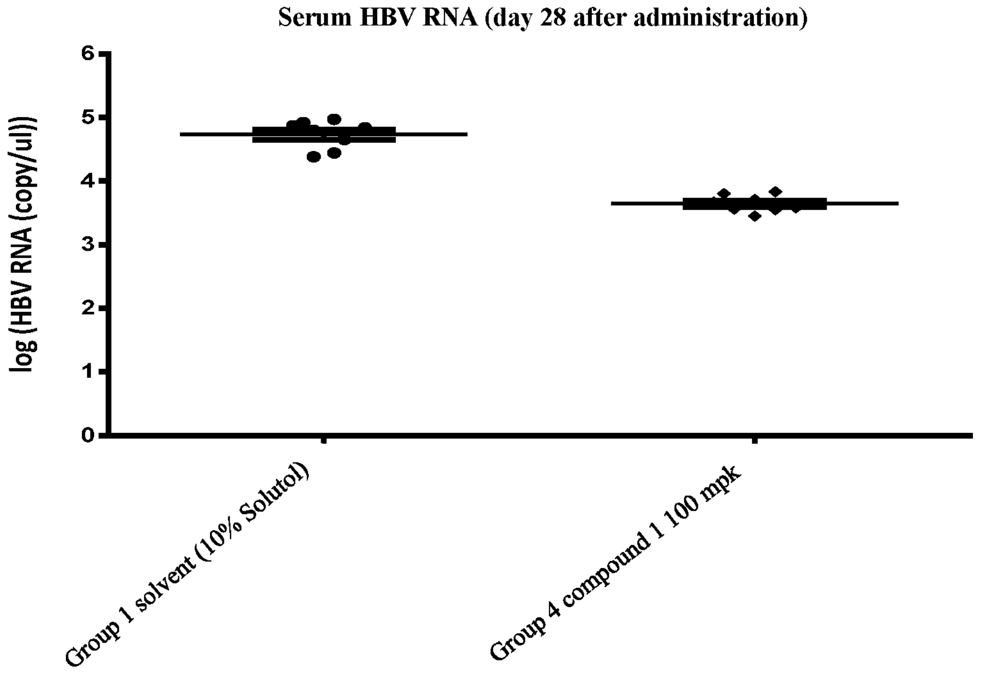
FIG. 4: the effect of the treatment of test compound on AAV/HBV mouse serum HBV RNA.

The content of HBV RNA in the serum of each group of mice is summarized in FIG. 4:

Compared with the solvent group (Group 1), after 28 days of dosage, the HBV RNA content in the serum of mice in the high dose (100 mpk) group of compound 1 decreased.

4) Pharmacokinetic Analysis of Test Compounds in AAV/HBV Model Mice

Figure 5:
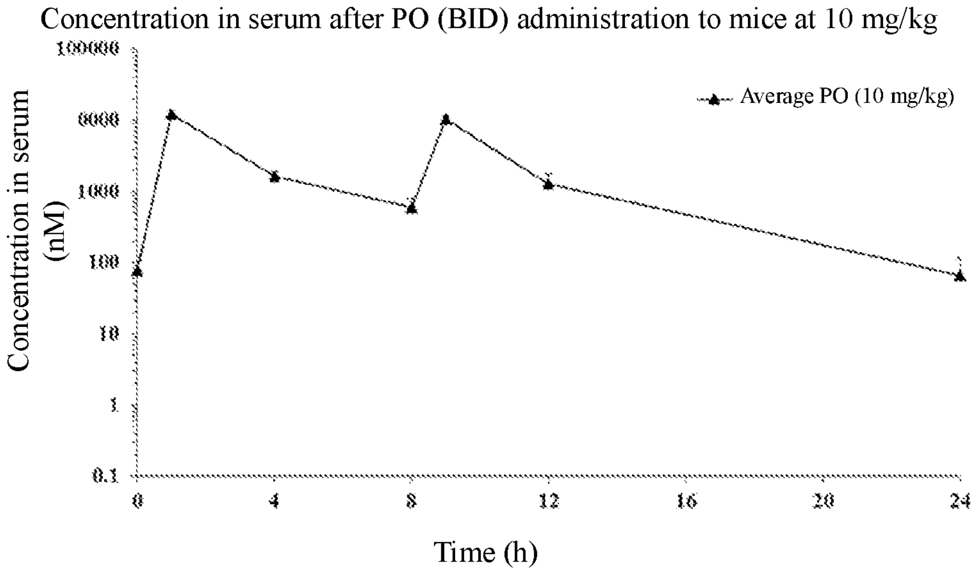
FIG. 5: concentration of test compound in mouse serum in AAV/HBV model.

The concentration of drugs in the serum of mice in group 2 is summarized in FIG. 5 and Table 6

On day 27, 0 hours after the first dosage (before dosage), 1, 4, 8, 9, 12, and 24, the average drug concentration in the mouse serum was 78, 122200, 1630, 605, 10300, 1280 and 66 nM, respectively. The drug absorption reached its peak 1 hour after dosage, the plasma half-life was 2.23 hours, and the $AUC_{0\text{-}inf}$ was 47600 nM·h.

TABLE 6

Metabolic analysis of test compounds in AAV/HBV model mice

| PK parameters | 10 mg/kg, BID |
|---|---|
| $T_{1/2}$ calculation time range | 9-24 |
| $C_{max}$ (nM) | 12200 |
| $T_{max}$ (h) | 1.00 |
| $T_{1/2}$ (h) | 2.23 |
| $T_{last}$ (h) | 24.0 |
| $AUC_{0\text{-}last}$ (nM · h) | 47300 |
| $AUC_{0\text{-}8}$ (nM · h) | 26000 |
| $AUC_{0\text{-}inf}$ (nM · h) | 47600 |
| $MRT_{0\text{-}last}$ (h) | 6.27 |
| $MRT_{0\text{-}inf}$ (h) | 6.36 |
| $AUC_{0\text{-}inf}/AUC_{0\text{-}last}$ (%) | 101 |

5) Mouse Health and Weight Monitoring

During the experiment, the health and weight of the mice were monitored regularly.

Figure 6:
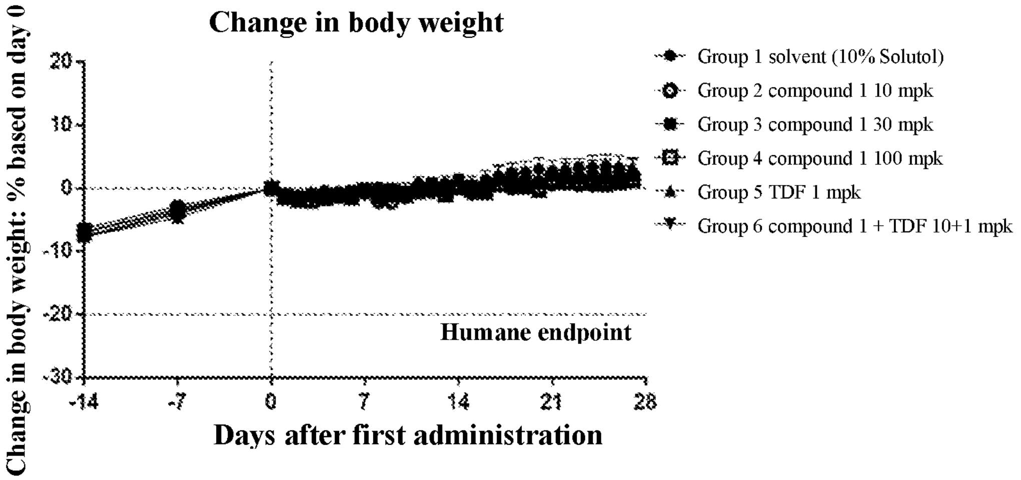
FIG. 6: weight change of mice in each group.

Comparing with body weight on day 0, the results of mouse body weight changes are summarized in FIG. 6:

The body weight of all mice remained stable during the expected period, and no significant drop was seen, and the mice were in good condition.

Note: From the −28th day to the 28th day, the weight change of the mice was recorded (the first day is changed to the day 0). The body weight on day 0 is used as a benchmark for comparison. According to IACUC regulations, a 20% weight loss is used as the humane endpoint. If a mouse loses more than 20% weight, it must be removed from the experiment.

7. Conclusion

Compared with the solvent control group, mouse serum and liver HBV DNA were significantly reduced after compound 1 treatment, and showed a dose-dependent trend in serum. After compound 1 and TDF are used in combination, the effect is significantly better than compound 1 single-drug therapy, showing a good combination drug effect. The body weight of the mice did not drop significantly during the entire experiment, indicating that the mice tolerated the test compound well.

8. Description

TDF in the experiment is replaced with ETV (entecavir), so that the in vivo antiviral effect of compound 1 and ETV is obtained, and the mouse serum and liver HBV DNA are significantly reduced and are superior to the single-drug therapy of compound 1.

Experimental Example 3: Compound 1 Combined with the Following Formula (IIb) Compound and Formula (IIIb) Compound on HBV Inhibitory Activity In Vitro (IIb)

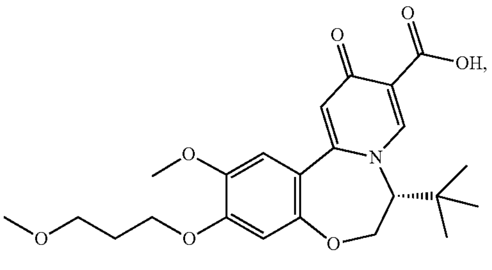

(IIIb)

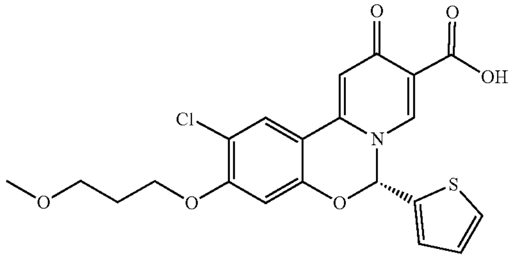

1. Experimental Materials

Cell line: HepG2.2.15 cells are constructed and provided by WuXi AppTec. The cell culture medium is DMEM/F12 medium supplemented with 2% fetal bovine serum, 2 mM glutamine, 1×non-essential amino acids, 100 U/mL penicillin and 100 g/mL streptomycin.

Reagents: The main reagents used in this study include FastStart Universal Probe Master (Roche, article number 04914058001), DNA extraction kit (Qiagen, article number 51162), CellTiter-Glo (Promega-G7573);

Instruments: The main instruments used in this study are 7900 real-time fluorescent quantitative PCR instrument (Applied Biosystems), multifunctional microplate reader (BioTek, Synergy2), QuantStudio™ 6 Flex System (Applied Biosystems)

Test compound: compound 1, compound of formula (IIb), compound of formula (IIIb).

2. Experimental Method 2.1 Anti-HBV Activity of Compound Single Agent 2.1.1 On the first day, HepG2.2.15 cells were seeded into a 96-well cell culture plate at a density of 60,000 cells/well, and then the cells were cultured overnight at 5% CO2 and 37° C. On the second day, the compound 1 and the compound of formula (IIb) and the compound of formula (IIIb) were diluted and added to a 96-well plate. Each combination was a three-fold plate. The cells were cultured under 5% CO2 and 37° C. for 3 days. The detection concentration of each compound is shown in Table 7. On the 5th day, a new culture medium containing the compound was replaced, and the supernatant was collected on the 8th day. The HBsAg in the supernatant was detected by ELISA, and the DNA in the supernatant was extracted at the same time, and the content of HBV DNA in the supernatant was detected by quantitative PCR. After collecting the cell supernatant, add CellTiter-Glo to detect cell viability.

TABLE 7

| []The concentration setting of test compound alone | | | | | | | | |
|---|---|---|---|---|---|---|---|---|
| Compound (nM) | 1 | 2 | 3 | 4 | 5 | 6 | 7 | 8 |
| Compound 1 | 1000.00 | 333.33 | 111.11 | 37.04 | 12.35 | 4.12 | 1.37 | 0.46 |
| Compound of formula (IIb) | 1000.00 | 333.33 | 111.11 | 37.04 | 12.35 | 4.12 | 1.37 | 0.46 |
| Compound of formula (IIIb) | 50.00 | 16.67 | 5.56 | 1.85 | 0.62 | 0.21 | 0.07 | 0.02 |

2.2 Anti-HBV Activity of the Compounds in Combination 2.2.1 On the first day, HepG2.2.15 cells were seeded into a 96-well cell culture plate at a density of 60,000 cells/well, and then the cells were cultured overnight at 5% $CO_2$ and 37° C. On the second day, different concentrations of compounds were added to treat the cells. Compounds were diluted in gradients, 7×7 concentration combinations, and 3 replicate plates were tested in parallel. The compound concentration tested for joint activity is based on the $EC_{50}$ value of each compound. The 7 concentration gradients are approximately: 2×, 1×, ½×, ¼×, ⅛×, 1/16× and 1/32×$EC_{50}$. The compound concentration of the combined activity test experiment is shown in Table 8, and the combination drug arrangement is shown in Table 9. On the 5th day, replace the fresh culture medium containing the compound. On the 8th day, the culture supernatant was collected, DNA was extracted, and the content of HBV DNA was detected by quantitative PCR. At the same time, CellTiter Glo reagent was used to detect cell viability and MacSynergy software was used to analyze the combined effect of the two drugs.

TABLE 8

| []Concentration setting of test compound combination | | | | | | | |
|---|---|---|---|---|---|---|---|
| | Concentrations (nM) | | | | | | |
| Compounds | 7 | 6 | 5 | 4 | 3 | 2 | 1 |
| Compound 1 | 12 | 6 | 3 | 1.5 | 0.75 | 0.375 | 0.188 |
| Compound of formula (IIb) | 6 | 3 | 1.5 | 0.75 | 0.375 | 0.188 | 0.094 |
| Compound of formula (IIIb) | 1.2 | 0.6 | 0.3 | 0.15 | 0.075 | 0.038 | 0.018 |

TABLE 9

| Combination medication arrangement of test compounds | | | | | | | | | | | | |
|---|---|---|---|---|---|---|---|---|---|---|---|---|
| Row | 1 | 2 | 3 | 4 | 5 | 6 | 7 | 8 | 9 | 10 | 11 | 12 |
| A | a0; b7 | a7; b7 | a6; b7 | a5; b7 | a4; b7 | a3; b7 | a2; b7 | a1; b7 | a0; b7 | a7; b0 | a0; b0 | BG |
| B | a0; b6 | a7; b6 | a6; b6 | a5; b6 | a4; b6 | a3; b6 | a2; b6 | a1; b6 | a0; b6 | a6; b0 | a0; b0 | BG |
| C | a0; b5 | a7; b5 | a6; b5 | a5; b5 | a4; b5 | a3; b5 | a2; b5 | a1; b5 | a0; b5 | a5; b0 | a0; b0 | BG |
| D | a0; b4 | a7; b4 | a6; b4 | a5; b4 | a4; b4 | a3; b4 | a2; b4 | a1; b4 | a0; b4 | a4; b0 | a0; b0 | BG |
| E | a0; b3 | a7; b3 | a6; b3 | a5; b3 | a4; b3 | a3; b3 | a2; b3 | a1; b3 | a0; b3 | a3; b0 | a0; b0 | BG |
| F | a0; b2 | a7; b2 | a6; b2 | a5; b2 | a4; b2 | a3; b2 | a2; b2 | a1; b2 | a0; b2 | a2; b0 | a0; b0 | BG |
| G | a0; b1 | a7; b1 | a6; b1 | a5; b1 | a4; b1 | a3; b1 | a2; b1 | a1; b1 | a0; b1 | a1; b0 | a0; b0 | BG |
| H | a0; b0 | a7; b0 | a6; b0 | a5; b0 | a4; b0 | a3; b0 | a2; b0 | a1; b0 | a0; b0 | a0; b0 | a0; b0 | BG |

Note:

a = compound 1, b = compound of formula (IIb) or compound of formula (IIIb); 0 means no compound, 1-7 means 7 concentrations.

3. Experimental Results

HepG2.2.15 cells were used to evaluate the inhibitory activity of compound 1 and compound of formula (IIb), compound 1 and compound of formula (IIb) in vitro against HBV. The inhibitory activity and cytotoxicity of the compound single drugs on HBV are summarized in Table 10. The inhibitory activity and cytotoxicity of the combined drugs on HBV are summarized in Tables 11-13.

TABLE 10

| Single-agent anti-HBV activity and cytotoxicity of compounds | | | |
|---|---|---|---|
| Test compound | HBV DNA $EC_{50}$ (nM) | HBsAg $EC_{50}$ (nM) | Cytotoxicity $CC_{50}$ (nM) |
| Compound 1 | 6.03 | >1000 | >1000 |
| Compound of formula (IIb) | 1.52 | 4.90 | >1000 |
| Compound of formula (IIIb) | 0.78 | 0.91 | >50 |

TABLE 11

Co-administration results of compound 1 and compound of formula (IIb) and compound of formula (IIIb) (99% confidence interval)

| Index | Joint | Synergy Index | Antagonism Index | Cytotoxicity | Result |
|---|---|---|---|---|---|
| HBV DNA | Compound 1 + Compound of formula (IIb) | 7.39 | 0 | NA | Additive effect |
| HBV DNA | Compound 1 + Compound of formula (IIIb) | 2.77 | −7.31 | NA | Additive effect |

Note:

Description of drug combination index: the absolute value of the index is less than 25, that is, the additive effect; the absolute value of the index is in the range of 25-50, that is, mild but clear synergy or antagonism; the absolute value of the index is in the range of 50-100, that is, moderate Synergistic or antagonistic effects may have important implications for in vivo effects. The absolute value of the index is in the range of >100, that is, a highly synergistic or antagonistic effect, which is likely to have important meanings in vivo.

TABLE 12

Cytotoxicity test average cell viability percentage (%) of Compound 1 combined with compound of formula (IIb)

| | | compound 1 | | | | | | | |
|---|---|---|---|---|---|---|---|---|---|
| Compound | Concentration (nM) | 12 | 6 | 3 | 1.5 | 0.75 | 0.375 | 0.1875 | 0 |
| Compound of formula (IIb) | 6 | 104.60 ± 3.29 | 110.65 ± 4.09 | 111.24 ± 2.77 | 108.30 ± 5.24 | 104.72 ± 10.16 | 107.32 ± 6.73 | 110.60 ± 1.62 | 111.27 ± 2.19 |
| | 3 | 96.23 ± 5.87 | 97.35 ± 1.48 | 99.53 ± 0.62 | 100.30 ± 2.29 | 100.39 ± 1.38 | 101.63 ± 2.84 | 101.72 ± 3.39 | 102.61 ± 4.65 |
| | 1.5 | 96.78 ± 2.78 | 100.15 ± 2.32 | 100.73 ± 3.01 | 99.76 ± 0.99 | 100.36 ± 2.65 | 98.83 ± 2.03 | 103.22 ± 3.95 | 104.15 ± 2.94 |
| | 0.75 | 100.70 ± 2.42 | 100.30 ± 0.58 | 101.31 ± 4.83 | 101.51 ± 2.28 | 106.55 ± 2.91 | 105.83 ± 3.84 | 104.84 ± 2.86 | 105.36 ± 1.65 |
| | 0.375 | 100.63 ± 3.24 | 100.83 ± 1.50 | 102.04 ± 1.76 | 102.87 ± 1.67 | 105.16 ± 2.52 | 103.29 ± 2.78 | 101.57 ± 2.93 | 102.39 ± 0.92 |
| | 0.1875 | 99.83 ± 5.27 | 100.86 ± 2.67 | 102.44 ± 2.66 | 101.94 ± 4.75 | 103.76 ± 3.85 | 102.48 ± 3.02 | 104.81 ± 3.98 | 101.98 ± 2.11 |
| | 0.09375 | 96.90 ± 4.27 | 95.50 ± 4.11 | 97.47 ± 2.36 | 96.64 ± 2.22 | 100.23 ± 2.47 | 97.60 ± 2.59 | 102.21 ± 0.84 | 101.23 ± 3.41 |
| | 0 | 102.08 ± 8.49 | 103.50 ± 6.49 | 104.39 ± 7.05 | 105.37 ± 8.80 | 106.91 ± 6.98 | 109.88 ± 3.82 | 109.29 ± 2.25 | 109.76 ± 1.63 |

TABLE 13

Cytotoxicity test average cell viability percentage (%) of Compound 1 combined with compound of formula (IIIb)

| | | Compound 1 | | | | | | | |
|---|---|---|---|---|---|---|---|---|---|
| Compound | Concentration (nM) | 12 | 6 | 3 | 1.5 | 0.75 | 0.375 | 0.1875 | 0 |
| Compound of formula (IIIb) | 1.2 | 110.95 ± 5.45 | 112.23 ± 4.72 | 113.70 ± 3.93 | 112.03 ± 1.06 | 110.25 ± 2.28 | 112.48 ± 2.80 | 112.88 ± 2.98 | 112.02 ± 2.99 |
| | 0.6 | 102.44 ± 4.62 | 103.05 ± 4.11 | 102.51 ± 6.12 | 103.62 ± 3.13 | 102.75 ± 3.52 | 105.55 ± 5.15 | 104.66 ± 4.40 | 103.50 ± 5.95 |
| | 0.3 | 99.66 ± 5.31 | 104.61 ± 4.31 | 103.85 ± 3.26 | 101.30 ± 5.94 | 101.01 ± 4.42 | 100.77 ± 5.22 | 105.16 ± 3.30 | 103.14 ± 6.14 |
| | 0.15 | 103.81 ± 5.15 | 108.76 ± 4.93 | 106.66 ± 4.55 | 107.26 ± 3.21 | 109.23 ± 3.36 | 110.09 ± 3.89 | 105.10 ± 6.11 | 105.68 ± 4.30 |
| | 0.075 | 103.12 ± 4.19 | 104.90 ± 3.36 | 105.13 ± 6.65 | 104.24 ± 3.69 | 108.04 ± 2.39 | 109.61 ± 3.02 | 105.89 ± 3.68 | 105.64 ± 3.61 |
| | 0.0375 | 104.13 ± 4.37 | 103.87 ± 5.20 | 104.20 ± 5.09 | 102.52 ± 3.80 | 102.13 ± 3.02 | 103.94 ± 1.76 | 104.85 ± 1.22 | 103.81 ± 4.25 |
| | 0.01875 | 100.86 ± 3.97 | 102.05 ± 2.76 | 102.06 ± 1.87 | 101.19 ± 2.25 | 101.90 ± 2.14 | 100.34 ± 4.33 | 101.23 ± 3.54 | 103.45 ± 4.84 |
| | 0 | 111.17 ± 2.41 | 112.45 ± 3.65 | 112.58 ± 5.37 | 111.96 ± 2.92 | 111.36 ± 5.07 | 112.42 ± 2.82 | 110.07 ± 5.45 | 112.83 ± 4.86 |

4. Experimental Results

In the HepG2.2.15 in vitro HBV infection model, the test compound inhibited HBV DNA in a dose-dependent manner; compound 1 and compound of formula (IIb), compound 1 and compound of formula (IIIb) showed the combined effect of additive effect, and the combination was in use No cytotoxicity was shown in the tested concentration. The test results support the combined application of compound 1 and the compound of formula (IIb), compound of formula (IIIb) and other hepatitis B surface antigen inhibitors in clinical treatment of chronic HBV infection.

5. Description

In accordance with the above embodiment, compound 1 is replaced with compound 2

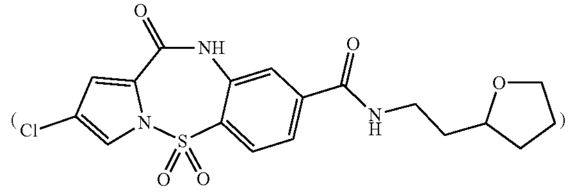 [SMILES: O=C(NCCC1CCCO1)c1ccc2c(c1)NC(=O)c1cc(Cl)cn1S2(=O)=O]

or compound 3

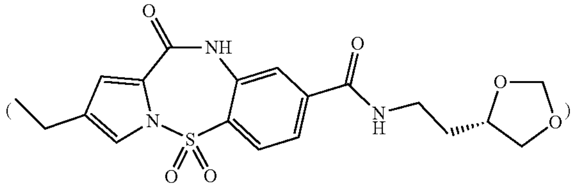 [SMILES: CCc1cc2n(c1)S(=O)(=O)c1ccc(C(=O)NCC[C@H]3COCO3)cc1NC2=O]

to obtain the results of the co-administration of compound 2 with the compound of formula (IIb) and with the compound of formula (IIIb) and the results of the co-administration of compound 3 with the compound of formula (IIb) and with the compound of formula (IIIb), both showing data results with additive effects and showing no cytotoxicity in the concentrations tested in combination use. The test results support the clinical combination use of the compounds such as compound 2 and compound 3 and the hepatitis B surface antigen inhibitors such as the compound of formula (IIb) and the compound of formula (IIIb) in the treatment of chronic HBV infection.

What is claimed is:

1. A pharmaceutical combination, consisting of a compound of formula (I) or a pharmaceutically acceptable salt thereof (I)

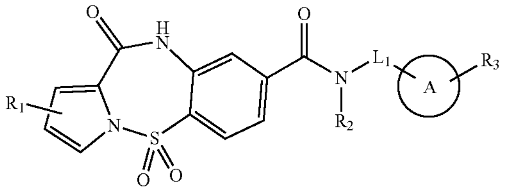

and any one of the following groups a to c of drugs:

a. a hepatitis B surface antigen inhibitor, b. a reverse transcriptase inhibitor, and c. a hepatitis B surface antigen inhibitor and a reverse transcriptase inhibitor, wherein, the compound of formula (I) is the following compound 1, compound 2, or compound 3:

1

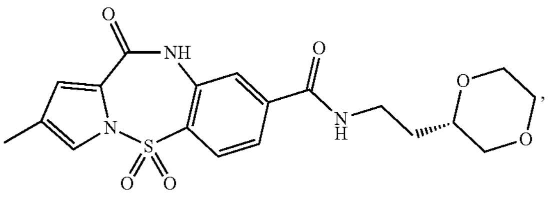

2

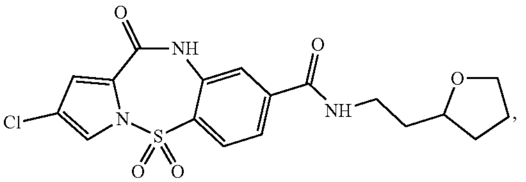

or

3

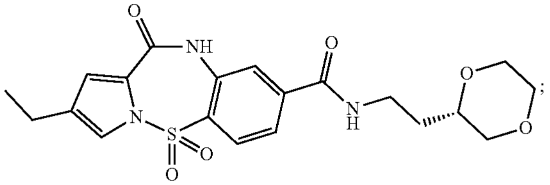

the hepatitis B surface antigen inhibitor is a compound of formula (IIb) or a compound of formula (IIIb):

(IIb)

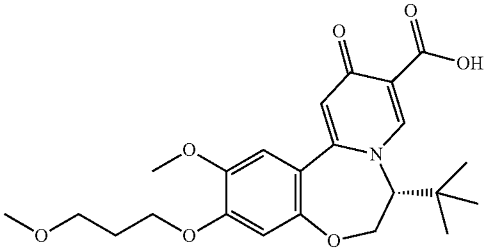

or (IIIb)

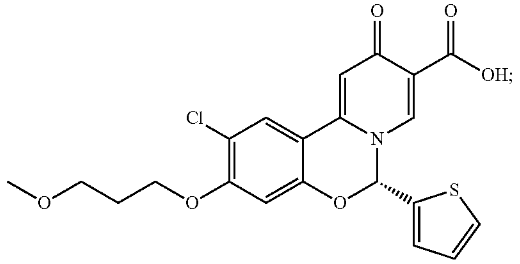

the reverse transcriptase inhibitor is selected from: lamivudine, adefovir dipivoxil, entecavir, tenofovir disoproxil fumarate and tenofovir alafenamide fumarate.

2. The combination according to claim 1, wherein the reverse transcriptase inhibitor is selected from: entecavir and tenofovir disoproxil fumarate.

3. The combination according to claim 1, wherein a pharmaceutical composition is prepared by mixing the compound of formula (I) or the pharmaceutically acceptable salt thereof and any one of the groups a to c of drugs as pharmaceutically active ingredients.

4. The combination according to claim 3, wherein the preparation of the pharmaceutical composition by mixing the pharmaceutically active ingredients is that a compound pharmaceutical composition is prepared by mixing two or three different drugs as pharmaceutically active ingredients.

5. The combination according to claim 1, wherein the compound of formula (I) or the pharmaceutically acceptable salt thereof and any one of the groups a to c of drugs, as pharmaceutically active ingredients, are separately prepared into pharmaceutical compositions, and the pharmaceutical compositions are further packaged separately and administered separately at the time of administration.

6. The combination according to claim 5, wherein the separate administrations comprise the administration of one or two of the pharmaceutical compositions, followed by the administration of another one or two of the pharmaceutical compositions, and the administration of two or three of the pharmaceutical compositions simultaneously.

7. A method for treating hepatitis B virus infection in a subject in need thereof, comprising: administering an effective amount of the combination according to claim 1 to the subject.

8. A pharmaceutical composition comprising the combination according to claim 1 and at least one pharmaceutically acceptable carrier and/or excipient.

9. A kit comprising the combination according to claim 1.

10. A method for treating hepatitis B in a subject in need thereof, comprising: administering an effective amount of the pharmaceutical composition according to claim 8 to the subject.

11. The combination according to claim 1, wherein the combination is any one of the following combinations I-IX:

I. a combination consists of the compound 1 and the tenofovir disoproxil fumarate;

II. a combination consists of the compound 1 and the entecavir;

III. a combination consists of the compound 1 and the compound of formula (IIb);

IV. a combination consists of the compound 1 and the compound of formula (IIIb);

V. a combination consists of the compound 2 and the compound of formula (IIb);

VI. a combination consists of the compound 2 and the compound of formula (IIIb);

VII. a combination consists of the compound 3 and the compound of formula (IIb);

VIII. a combination consists of the compound 3 and the compound of formula (IIIb);

IX. the combination consists of the compound 1 and the tenofovir alafenamide fumarate.

12. The combination according to claim 1, wherein the combination shows an addition effect on the inhibitory activity of HBV or shows better anti-HBV efficacy than single-drug therapy.

13. The combination according to claim 11, wherein the combination shows an addition effect on the inhibitory activity of HBV or shows better anti-HBV efficacy than single-drug therapy.

14. The combination according to claim 1, the combination shows a synergistic effect in treating HBV.

15. The combination according to claim 11, wherein the combination shows a synergistic effect in treating HBV.

16. The combination according to claim 11, wherein the combination I shows a synergistic effect in treating HBV.

17. The combination according to claim 11, wherein the combination II shows a synergistic effect in treating HBV.

18. The combination according to claim 11, wherein the combination IX shows a synergistic effect in treating HBV.

19. The combination according to claim 11, wherein the combination IV shows a synergistic effect in treating HBV.

* * * * *